United States Patent
Gorokhovsky et al.

(10) Patent No.: US 9,150,951 B2
(45) Date of Patent: Oct. 6, 2015

(54) WEAR RESISTANT VAPOR DEPOSITED COATING, METHOD OF COATING DEPOSITION AND APPLICATIONS THEREFOR

(75) Inventors: Vladimir Gorokhovsky, Bozeman, MT (US); Brad B. Heckerman, Missoula, MT (US); Yuhang Cheng, Missoula, MT (US)

(73) Assignee: G & H Technologies LLC, Missoula, MT (US)

(*) Notice: Subject to any disclaimer, the term of this patent is extended or adjusted under 35 U.S.C. 154(b) by 0 days.

(21) Appl. No.: 13/103,871

(22) Filed: May 9, 2011

(65) Prior Publication Data

US 2012/0006785 A1    Jan. 12, 2012

Related U.S. Application Data

(62) Division of application No. 11/804,433, filed on May 17, 2007, now Pat. No. 7,939,172.

(60) Provisional application No. 60/801,142, filed on May 17, 2006.

(51) Int. Cl.
| | |
|---|---|
| *C23C 14/02* | (2006.01) |
| *C23C 14/06* | (2006.01) |
| *C23C 16/02* | (2006.01) |
| *A61B 17/16* | (2006.01) |
| *A61C 3/02* | (2006.01) |
| *A61C 5/02* | (2006.01) |

(52) U.S. Cl.
CPC ............. *C23C 14/024* (2013.01); *C23C 14/025* (2013.01); *C23C 14/0605* (2013.01); *C23C 16/0272* (2013.01); *A61B 17/1615* (2013.01); *A61B 2017/1602* (2013.01); *A61C 3/02* (2013.01); *A61C 5/023* (2013.01); *Y10T 428/24975* (2015.01); *Y10T 428/252* (2015.01); *Y10T 428/265* (2015.01); *Y10T 428/30* (2015.01)

(58) Field of Classification Search
CPC .... C23C 14/325; C23C 28/044; C23C 28/42; C23C 14/024; A61C 3/02
See application file for complete search history.

(56) References Cited

U.S. PATENT DOCUMENTS

| | | | | |
|---|---|---|---|---|
| 1,957,602 | A * | 5/1934 | Kylberg | 451/191 |
| 4,653,373 | A * | 3/1987 | Gerber | 83/697 |
| 5,707,748 | A * | 1/1998 | Bergmann | 428/469 |
| 6,547,562 | B2 * | 4/2003 | Kumar | 433/165 |
| 2002/0102400 | A1 * | 8/2002 | Gorokhovsky et al. | 428/336 |

OTHER PUBLICATIONS

Miyakawa (Vacuum 73 (2004) 611-617).*

* cited by examiner

*Primary Examiner* — Joel Horning
(74) *Attorney, Agent, or Firm* — Jean Kyle

(57) ABSTRACT

A low friction top coat over a multilayer metal/ceramic bond-coat provides a conductive substrate, such as a rotary tool, with wear resistance and corrosion resistance. The top coat further provides low friction and anti-stickiness as well as high compressive stress. The high compressive stress provided by the top coat protects against degradation of the tool due to abrasion and torsional and cyclic fatigue. Substrate temperature is strictly controlled during the coating process to preserve the bulk properties of the substrate and the coating. The described coating process is particularly useful when applied to shape memory alloys.

15 Claims, 19 Drawing Sheets

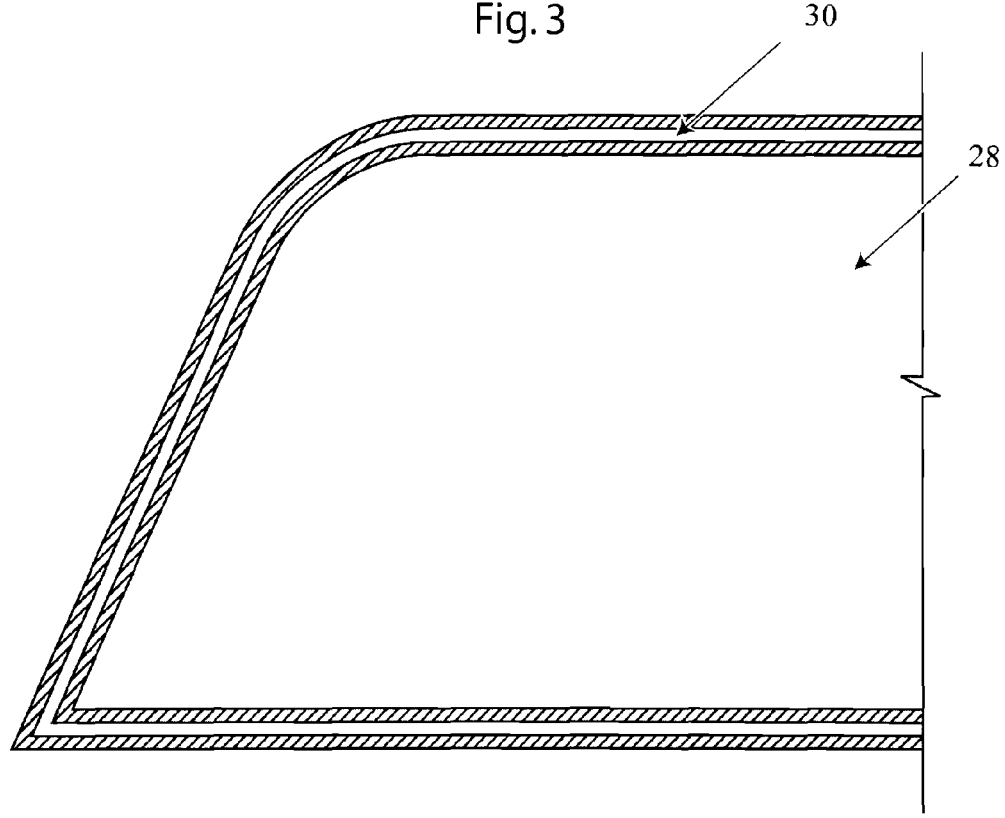

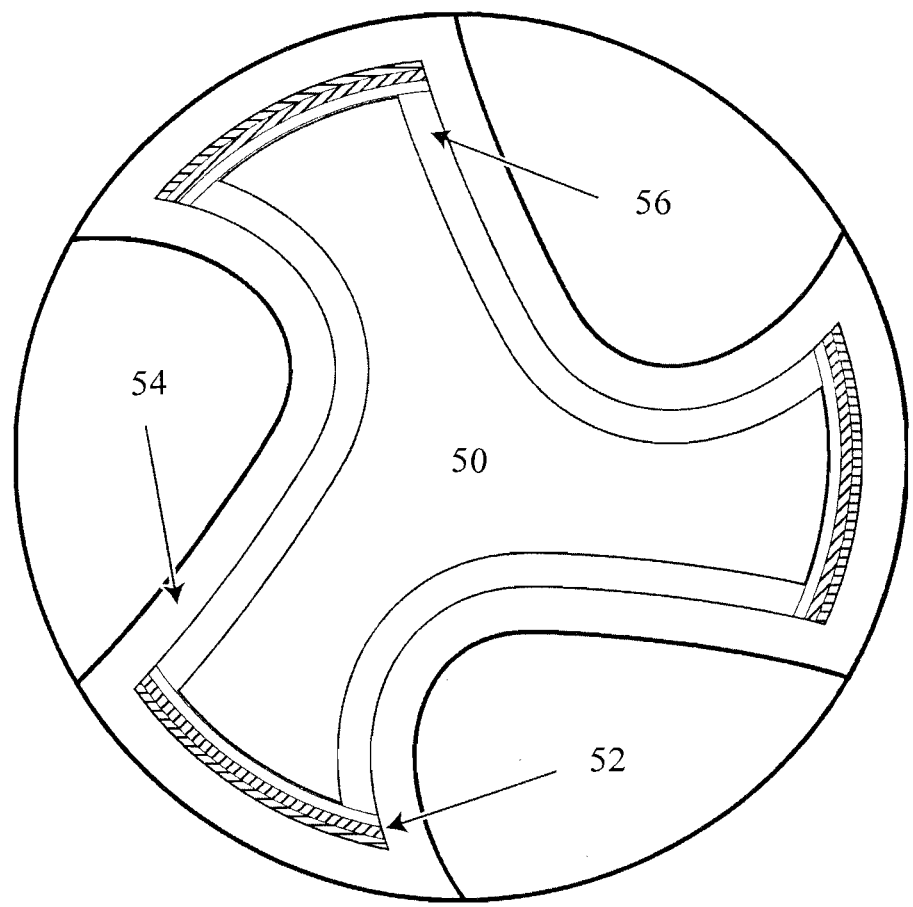

WEAR RESISTANT VAPOR DEPOSITED COATING, METHOD OF COATING DEPOSITION AND APPLICATIONS THEREFOR

CROSS-REFERENCE TO RELATED APPLICATIONS

This application is a divisional of U.S. application Ser. No. 11/804,433, filed May 17, 2007, now U.S. Pat. No. 7,939,172, which claims the benefits of U.S. Provisional Application No. 60/801,142, filed May 17, 2006, the disclosures of which are hereby incorporated by reference in their entirety including all figures, tables and drawings.

FIELD OF INVENTION

This invention relates to hard, wear resistant coatings vapour deposited over a metallic or non-metallic surface, in particular, the invention relates to a coating to be deposited on rotary tools having cutting edges utilized in industrial, medical and dental cutting, and form scraping, and is more particularly directed to improvements in blades and rotary cutting instruments.

BACKGROUND OF THE INVENTION

Hard wearing surfaces are in common use in various industries, and such hard wearing surfaces are frequently obtained by coating the surface of a tool made of steel or similar metal, or other hard, enduring material, with a layer of hard wearing ceramic substance, such as carbides, nitrides and carbonitrides, or providing a hard microcrystalline diamond coating. There are known methods for obtaining hard wearing coatings, such as for example, having a coating of diamond particles in combination with a carbide or nitride layer and then filling the gaps between the abrasive particles with a softer intermetallic compound. Another known method is vapour deposition of hard-wearing ceramic materials from plasma or by utilizing molten ceramic substances. Hard wearing surfaces for use on medical, surgical and dental tools have additional requirements, as such surgical and dental tools need to be frequently sterilized, hence medical tools have to be corrosion resistant.

A device for yielding hard ceramic surfaces by cathodic arc plasma deposition is described in U.S. Pat. No. 4,851,095, issued to M. A. Scobey et al. on Jul. 25, 1989. The apparatus of Scobey et al. utilizes a high intensity ion flux. Vapour deposition of a hard ceramic material, such as titanium or zirconium nitride, on a stainless steel or titanium surface by utilizing a molten evaporant and a hollow cathode, is described in U.S. Pat. No. 5,152,774, issued to W. A. Schroeder on Oct. 6, 1992. The vapour deposition of Schroeder is conducted at relatively low temperature, thus the substrate will have lost little of its initial high strength properties, however, the requirement of low surface roughness of the deposited layer is not addressed by U.S. Pat. No. 5,152,774. In U.S. Pat. No. 4,981,756, issued to H. S. Rhandhawa on Jan. 1, 1991, a method is taught to coat surgical tools and instruments by cathodic arc plasma deposition. The ceramic coating obtained by this technology is a nitride, carbide or carbonitride of zirconium or hafnium, in a single layer of 3-10 µm thickness. U.S. Pat. No. 4,981,756 also refers to various publications describing known equipment for obtaining hard-wearing surfaces by cathodic arc plasma deposition. U.S. Pat. Nos. 5,940,975 and 5,992,268 issued to T. G. Decker et al. on Aug. 24, 1999 and Nov. 30, 1999, respectively, teach hard, amorphous diamond coatings obtained in a single layer on thin metallic blades or similar metallic strips utilizing filtered cathodic are plasma generated by vaporizing graphite. It is noted that no interlayer is formed between the blade surface and the deposited amorphous diamond coating.

The grain size of deposits obtained in conventional cathodic plasma are methods may range between 0.5 to 10 µm. Any post-deposition heat treatment which may be required to maintain maximum hardness of the substrate's core metal, may lead to internal stresses in the coating due to differences in the grain size, and can eventually lead to abrasion, spalling, crack formation, grain separation, surface fractures, uneven edges and rough surfaces, and the like, which can drastically reduce the wear resistance and durability of surgical instruments and dental tools. None of the above discussed methods are concerned with even grain size and surface structure, and low micro-roughness of the vapour deposited hard, ceramic coatings, which have particular importance for dental and surgical tools, and in other applications where straight, sharp, even and nick-free edges are essential requirements.

Users desire cutting blades with sharp edges possessing long life and corrosion resistance. Typically, blades are initially sharpened to form a wedge shaped cutting edge and re-sharpened as needed, except in the case of razor blades which cannot be re-sharpened. Sharpness of a cutting blade is measured in terms of "ultimate tip radius", which is different depending on the application. For kitchen knives, rotary cutters, and similar cutting instruments, ultimate tip radius may be several thousand Angstroms. In agricultural implements incorporating rotary blades that cut through the soil, axes, and in chisels, the cutting edge radius may be expressed in microns or even in millimeters rather than Angstroms. Shaving razor blades ordinarily have ultimate tip radii of about 1,500 Angstroms or less. This radius usually includes a layer of hard material coating applied to the wedge shaped base material of the razor blade. A self-sharpening blade having a cutting edge with different hardness and wear resistance on opposite sides of the blades, provided by applying different coating layers on opposite sides of the blade is described in U.S. Pat. No. 6,105,261, issued to Ecer on Aug. 22, 2000. This invention provides a solution to the problem of the cutting edge dulling by providing self-sharpening cutting edges with different hardness and wear resistance on opposite sides of the edge while both sides have micro-hardness and wear resistance significantly greater than the substrate metal. Cutting areas are kept sharp longer with this method especially in such adverse environments as in dental/surgical applications, use as saw blades and scrapers and in the construction industry. The disadvantage of this approach is that more intensive wear on one side of the edge leaves the hard layer unsupported which eventually results in a failure of the more brittle hard layer by fracturing. The soft side of the cutting edge has a higher wear rate which affects the support of the brittle thin film coating on the opposite side.

Coatings such a TiN, Ti(CN), or (TiAl)N deposited onto the blade edge region of a steel knife blade blank by a cathodic arc process with simultaneous heating and rotation of the blade blank relative to the deposition sources are described in U.S. Pat. No. 5,724,868, issued to Knudsen et al. The blade edge region may be sharpened or unsharpened prior to deposition of the coating material. If the blade edge region is unsharpened prior to deposition, it is thereafter sharpened, preferably on one side only. An improvement of this method was proposed in U.S. Pat. No. 6,656,186, issued to Meckel et al. and includes depositing different coatings with different hardness on both sides of the blades adjacent to cutting edge.

However, in operation the material on the softer side of the blade suffers greater wear and is not be able to support the harder coating on the opposite side of the blade. Further, this method as well as the methods described previously, does not address issues of friction and galling properties of the coated surface on the cutting tool.

It is known to coat dental tools and surgical instruments with titanium nitride and titanium, wherein the coating is obtained by conventional cathodic arc deposition applied to corrosion resistant stainless steel substrates. The cutting surfaces of such medical tools need to be smooth, as well as hard-wearing to prevent trapping and retaining materials which can be harmful to the patient. Hence, another requirement is that the cutting edges be very straight, sharp and nick-free to avoid damage to the surrounding flesh and skin during dental or surgical treatment. There are known methods described, wherein the cutting tips of surgical instruments made of steel have been sand-blasted and then coated with a hard-wearing ceramic composition, however this method can, and is likely to, increase surface roughness and unevenness, rather than eliminate it. The main disadvantage of these methods is that the hard or even superhard coating with micro-hardness in excess of 20 GPa is deposited on relatively soft substrate surface made of steel or other alloy having micro-hardness less than 8 GPa. That creates a so-named egg-shell effect when the failure of the hard and brittle thin film coating is due to mechanical deformation of underlying soft substrate material.

The duplex technology utilizing ionitriding followed by thin film coating was developed to improve the wear resistance to bridge the mechanical properties between the soft substrate metal and hard coating. This technology however is limited to selective types of steels and metal alloys due to poor adhesion of the hard coatings to most ionitrided metallic materials.

In U.S. Pat. No. 6,617,057 issued to Gorokhovsky a multilayer cermet coating is described which employs alternating metal and ceramic layers. This coating architecture provides high hardness and at the same time secures necessary elasticity and ductility so the brittle hard ceramic layer will not fail due to bending and deformation of the substrates while the tool is in operation. Using the cathodic arc technology to create the multilayer coating eliminates the problems of surface roughness and increased radius of cutting edge. The coatings produced have a moderate hardness and wear resistance but exhibit relatively high friction and high galling properties. These cermet coatings have relatively higher friction in comparison with carbon diamond like (DLC) and related coatings.

There is a need for a method which can provide a fine grained, hard wearing ceramic surface that has low microroughness, sharp even edges, and has a low friction co-efficient and presents anti-galling properties. In preferred cases, the coating should also withstand post-deposition heat treatment without degradation of the coating.

All patents, patent applications, provisional patent applications and publications referred to or cited herein, are incorporated by reference in their entirety to the extent they are not inconsistent with the teachings of the specification.

SUMMARY OF THE INVENTION

An object of invention is to obtain a stable cutting edge consisting of multilayer coating with different architectures on both sides of the blade of a rotary tool. These coatings primarily focus on reduction of stickiness and friction of the rotary instruments to reduce torsion fatigue when they come in contact with their counterpart. Other properties of the surface engineered instruments are dedicated for improvement of coating toughness, abrasion wear resistance and corrosion resistance.

The coating of the subject invention generally comprises a top wear-resistant low friction anti-galling segment overlaying a bottom multilayer bondcoating cermet segment which accommodates the internal stresses in the top segment and secures the highest toughness of the entire coating system. A hard case can be optionally created on the surface of the bulk metal substrate under the bondcoating segment by ionitriding or carburizing, which reduces the gradient of mechanical properties between the hard ceramic coating and the relatively soft metallic substrate. In addition the ionitrided or carburized layer serves as a hard foundation to support the thin low friction top segment coating against mechanical deformation of the soft base metal material. The top coating segment comprises of a near amorphous matrix composed of carbon, metal doped carbon, hydrogenated carbon having a mixture of diamond like and graphite like interatomic bonding. The amorphous matrix can be optionally filled with nanocrystalline refractory ceramic phases such as carbides, nitrides, silicides, borides, oxides, carbo-borides and a like compounds with size of the crystals ranging from 0.5 to 100 nm. The coefficient of friction of the top segment coating is less than 0.3. The bottom multilayer cermet coating segment has a fine columnar structure which contributes to the extremely high adhesion and flexural rigidity while the top layer reduces friction and galling forces and contributes to the high wear resistance of the coating. This coating architecture is especially beneficial for rotary instruments for protection against abrasive wear, reducing torsional friction, and improving fatigue life. This not only improves the durability of the instrument, but also reduces the negative effect of cutting on counterparts, which is especially important in the case of dental and medical instruments. A cutting tool with the coating of this invention leaves a smooth surface after cutting without holes and disruptions created by chunks of materials being removed due to scuffing induced by stickiness of the cutting material to the surface of the cutting tool.

According to one embodiment of the present invention a wear resistant, composite vapour deposited metal ceramic coating is provided on a substrate capable of electrical conduction. The coating comprises a bottom bond segment composed of a metal-ceramic multilayer architecture and a top low friction anti-galling nanostructured segment. The bottom bond segment includes at least one metallic layer selected from the group consisting of titanium, chromium, vanadium, aluminum, molybdenum, niobium, tungsten, hafnium, zirconium and alloys thereof and having a metallic layer thickness. The bottom bond segment further includes at least one ceramic layer selected from the group consisting of nitrides, carbides, carbonitrides, oxynitrides, borides, carboborides, borocarbonitrides, silicides, borosilicides and combinations thereof. The bottom bond segment coating has a thickness greater than 0.01 μm, a micro-roughness of less than the total thickness of the uppermost ceramic layer, and a micro-hardness in excess of 20 GPa. The top low friction anti-galling coating segment includes amorphous diamond like matrix composed of the group of elements consisting of carbon, boron, silicon, nitrogen, hydrogen, oxygen and transition metals optionally filled with nanocrystalline refractory ceramic phase embedded in the amorphous matrix. The amorphous matrix can further include diamond-like interatomic bonding. The nanocrystalline refractory ceramic phase comprises carbides, borides, silicates, nitrides and oxides. The thickness of the top segment coating is greater than 0.01 μm.

The size of refractory ceramic nanocrystals ranging from 0.5 to 100 nm. The coefficient of friction of the top coating segment is less than 0.3.

The substrate can be of steel or titanium alloys. The steel substrate is preferably made from high chromium steel such as, for example, 440 series and 17-4 series. The substrates made of titanium alloys include Nickel-Titanium based alloys. The steel can have an ion nitrided, ion implanted, oxi-nitrided or carburized surface layer between it and the bottom bond coating segment.

A process is provided for producing a wear resistant, low friction, composite vapour deposited metal-ceramic coating on the surface of the substrate capable of electrical conduction. The surface of a substrate is first cleaned then placed into the vacuum chamber of a vapor depositing device capable of providing controlled electric and magnetic fields where the substrate is coated with at least one metallic layer and at least one ceramic layer then coated with a top coat. Optionally, the surface of the substrate is treated in a ionitriding, oxy-nitriding, ion implantation or carburizing process step. The process comprises the following steps:

i) providing a substrate capable of electrical conduction, having a surface and cleaning said surface with at least one cleaning method selected from the group consisting of chemical cleaning, electrolytic cleaning, grinding, polishing, tumbling and ion bombardment to produce a cleaned substrate;

ii) placing said cleaned substrate into the vacuum chamber of a vapour depositing device capable of providing controlled electric and magnetic fields, and having a substrate holder capable of holding at least one substrate, a target electrode holder, and an inlet for a vapour depositing atmosphere of controlled composition and pressure;

iii) providing a target electrode within said vacuum chamber, of at least one of the metals selected from the group consisting of titanium, chromium, vanadium, aluminum, molybdenum, niobium, tungsten, hafnium, zirconium, and alloys thereof;

iv) providing a vapour depositing atmosphere within said vacuum chamber, comprising at least one of the gases selected from the group consisting of argon, nitrogen, methane or other hydrocarbon gas, 3-methylsilane (3MS) gas or oxygen;

v) optionally, treating said surface of said substrate in an ionitriding, oxy-nitriding, ion implantation or carburizing process step;

vi) applying electric potential and a filtering magnetic field in an atmosphere within said vacuum chamber, to obtain a first, vapour deposited metal layer selected from the group consisting of titanium, chromium, vanadium, aluminum, molybdenum, niobium, tungsten, hafnium, zirconium, and alloys thereof, on said surface of said substrate;

vii) applying electric potential and a filtering magnetic field in an atmosphere within said vacuum chamber, containing at least one of the gases selected from the group consisting of nitrogen, methane or other hydrocarbon gas, 3MS gas or oxygen, to obtain a second, vapour deposited layer of a ceramic compound of a metal selected from the group consisting of titanium, chromium, vanadium, aluminum, molybdenum, niobium, tungsten, hafnium, zirconium, and alloys thereof, on said first layer deposited on said surface of said substrate;

viii) repeating steps vi) and vii), thereby obtaining multiple vapour deposited metal layers and multiple vapour deposited ceramic compound layers on said surface of said substrate;

ix) applying electric potential and a filtering magnetic field in an atmosphere within said vacuum chamber, containing at least one of the gases selected from the group consisting of methane or other hydrocarbon, or 3MS gas to obtain a top low friction vapour deposited segment coating containing metal components selected from the group consisting of titanium, chromium, vanadium, aluminum, molybdenum, niobium, tungsten, hafnium, zirconium, and alloys thereof, and carbon based DLC layers;

x) removing said substrate having multiple vapour deposited metal and ceramic layers on said substrate surface, from said vapour depositing device; and xi) optionally, heat treating the obtained metal and ceramic vapour deposited coating layers and a low friction vapor deposited top layer on said substrate surface.

Alternatively, a blank (unsharpened) substrate can be coated with a cermet bondcoating segment, then sharpened. The sharpened surface is then cleaned and coated with a low-friction, anti-galling top coat. The method comprises the steps of:

i) providing a blank (unsharpened) substrate capable of electrical conduction by applying at least one finishing method selected from the group consisting of sandblasting, chemical cleaning, electrolytic cleaning, grinding, polishing, vibratory tumbling and ion etching to produce a cleaned substrate;

ii) depositing a first hard thin film cermet bondcoating segment on a blank substrate by vapor deposition process;

iii) sharpening the substrate by grinding, cutting, twisting, and/or polishing for developing at least one side of at least one cutting edge;

iv) cleaning the substrate by applying at least one finishing method selected from the group consisting of sandblasting, chemical cleaning, electrolytic cleaning, grinding, polishing, vibratory tumbling and ion etching to produce a cleaned substrate;

v) depositing a second low friction anti-galling thin film nanocomposite top coating segment on a top of substrate by vapor deposition process.

The following optional step can be introduced between step ii) and step iii); if required or preferred, heat treating the obtained vapour deposited first segment coating deposited on said substrate surface.

The following additional optional step can be introduced between step iv) and step v); if required or preferred, ionitriding or ion implantation prior to deposition of top segment low friction anti-galling coating layer.

The distinguishing feature of the coating deposition steps, when applied to the substrates made of thermally sensitive alloys, is that it exposes the substrate to the plasma deposition in a periodic pulsing manner with depositing time, when the substrate is exposed to the vapour plasma deposition process followed by pause time, when plasma environment is removed from contact with the substrate and the substrate is cooled by means of radiation cooling and conduction cooling. The thermal sensitive substrates are defined by their sensitivity to being heated to the temperatures above a certain value critical for this particular alloy causing them to lose some of the important functional properties, which may or may not be further restored by subsequent heat treatment.

BRIEF DESCRIPTION OF THE DRAWINGS

FIG. 3 is a schematic drawing of the cross-section of a rotary instrument blade with the coating design having two sides with multilayer cermet coating.

FIG. 8c is a schematic drawing of the cross-section of an endofile with a coating similar to that shown in FIG. 8b, but with a duplex bottom segment coating on the inner side of the flute.

Figure 1:
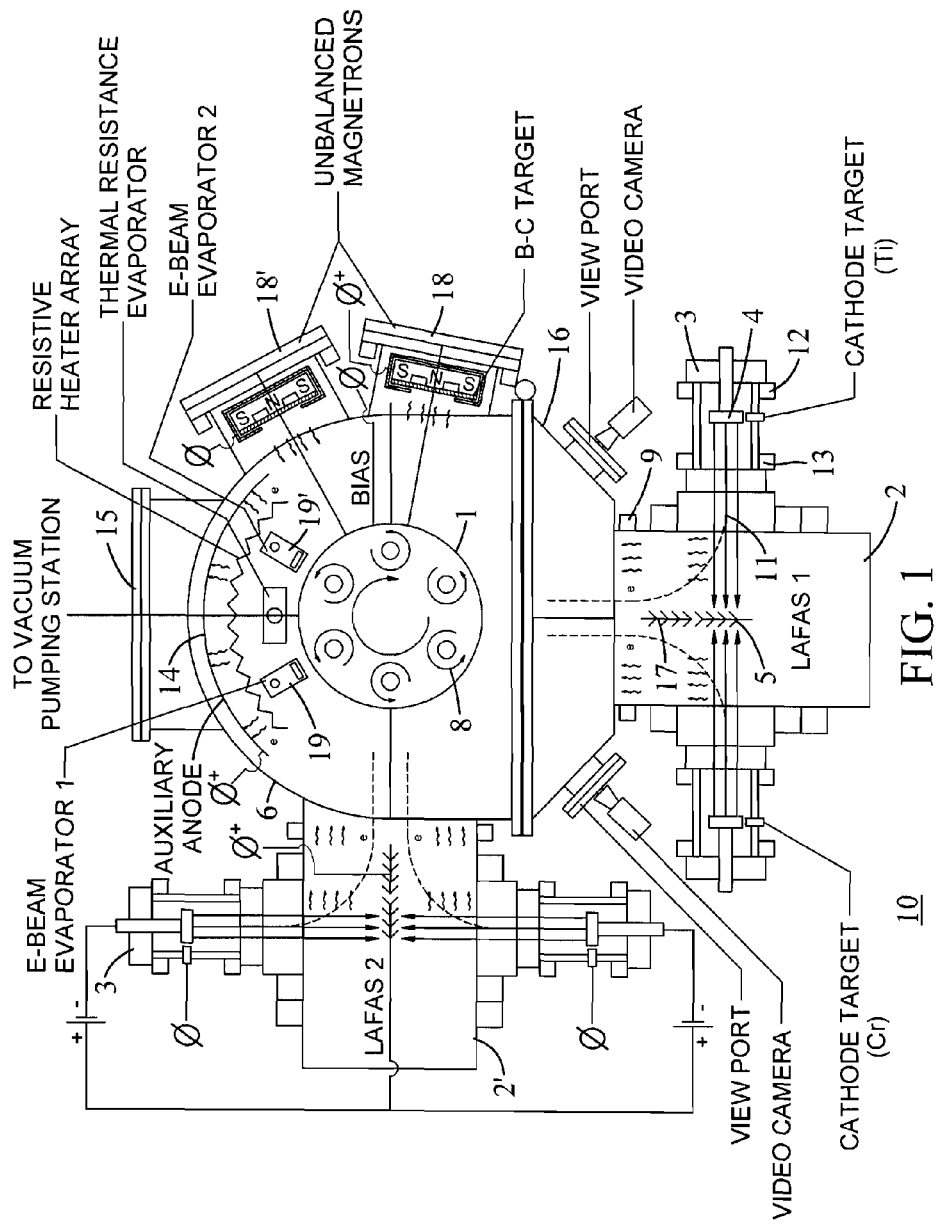
FIG. 1 is a schematic drawing of the surface engineering device utilized in this invention.

A detailed description of the preferred embodiments of the invention will follow, illustrated by working examples.

DETAILED DESCRIPTION OF THE INVENTION

For the sake of clarity, definition of what is understood by some of the terminology used in the discussion of the preferred embodiments of the present invention is provided below.

"Substrate" is understood to mean a three dimensional body providing the surface on which the vapour species is deposited. Only a portion of the surface, usually the surface in the proximity of one end of the substrate body, is utilized as the depositing surface, and the other end of the body of the substrate is attached to or is supported by, a substrate mount or holder. It is preferred that the portion of the surface on which the deposit is to be obtained, has close to uniform temperature, while the rest of the substrate may be in a temperature gradient.

"Plasma" is considered to mean an atmosphere of low pressure and high temperature, containing a mixture of ionized gases and metal vapor. Not all the gases in the plasma are ionized, but it is usual that the species to be deposited is ionized. The components of plasma often include argon or similar inert gases, both in the atomic state and in an ionized state.

"Even surface" in the context of a deposited layer surface is understood to mean that the average distance between the peaks of the deposited surface and the valleys of the deposited surface, is small. In other words, the micro-roughness of an evenly deposited surface is considered to be low.

In one embodiment of the present invention multiple layers of a controlled thickness of a metal and of a hard-wearing ceramic compound of the same metal, are deposited in successive steps on a conductive substrate surface, usually stainless steel, titanium alloy, or other appropriate metal. It is preferred that at least two pairs of the metal layer and the hard-wearing ceramic layer are deposited on the steel substrate. The number of layer pairs constituting the coating may range from 2 to as high as 100s, depending on the desired coating thickness, and on economic considerations. The bottom bondcoating segment can have at least one pair of a metal layer and a ceramic layer having a common metal ion component. The bottom bondcoating segment can comprise a multiplicity of pairs of metal and ceramic layers having a common metal ion component. The composite vapor deposited metal-ceramic coating can be heat treated subsequent to deposition. The thickness of the bottom bond coating segment can range between 0.01 μm and 30 μm. The vapor deposited metal-ceramic coating can comprise a portion of a surface of a dental tool, a surgical tool or a cutting tool. The bottom bond coating segment can comprise one side of the blade, or both sides, while the top low friction segment can overlay both sides of the blade. The top coat, low friction layer can be deposited over the multilayer bondcoat. The thickness of the top low friction anti-galling coating segment can range between 0.01 μm and 30 μm. The total coating thickness can range between 0.02 μm and 40 μm.

Several different coating deposition processes either associated with physical vapor deposition (PVD) or chemical vapor deposition (CVD) or hybrid PVD+CVD technology can be used for deposition of the coating of the subject invention. The protective or functional thin coatings on dental and medical instruments are aimed to improve cutting efficiency, durability and bio-compatibility. Conventional CVD technology requires high temperature for decomposition of metal-organic, halide or hydrocarbon based precursors, which makes its applications restricted to high temperature substrates. Using low pressure plasma assisted CVD processes (PACVD) allows for reduced substrate temperatures during the coating deposition stage, but is still restricted to a limited number of elemental compositions and coating architectures. PVD processes such as magnetron sputtering and electron beam evaporation are widely used for coating deposition on cutting tools. Electron beam PVD technology (EBPVD) can provide a theoretically unlimited evaporation rate of a wide variety of different materials: metals, ceramics, cermets, both conductive and dielectric materials, but the ionization rate of the EBPVD metal vapor flow is extremely low (<0.1%) which require ion beam assistance to achieve dense coatings with acceptable adhesion and fine microstructure.

Sputtered multilayer coating stacks using multiple sources within the same system, are used routinely for industrial manufacturing on any substrate that can handle vacuum and plasma exposure. To reduce cross contamination from one source to another either zoned vessels or other means to isolate a source from adjacent neighbors are common. Sputtering in conjunction with a reactive gas can yield a myriad of coatings with a wide variety of elemental compositions and architectures. Matrix sputter source structures using 2 or more part targets are possible that yield various composition combinations simultaneously. The magnetron sputtering process is capable of generating an atomized vapor flow from targets having low electrical conductivity. Using a split target of graphite or boron carbide with a metal segment made of molybdenum, titanium or other transition metals allows for deposition of Me doped diamond-like and boron carbide based coatings. Co-sputtering (2 sources with different targets on each) yield variability of composition over the course of a given process. By having various targets adjacent or oriented at roughly 45° to 90° in respect to the substrate surface and varying the power to each source separately it is possible to yield not only different thickness but also different compositions within a thin film. The primary issues with sputtering are low productivity (rate of deposition) and necessity of using large concentrations of argon as a sputtering gas. Low ionization rates on the order of 1-3% in magnetron sputtering flows reduce the intensity of ion bombardment assistance during coating deposition processes resulting in coarse coating morphology and fair adhesion. To improve coating structure, adhesion toughness, and functional properties, a number of different processes were introduced. Unbalanced magnetron methods are successful in attaining higher ionization (up to 10-15%) in comparison to conventional magnetron sources but it is still too low for substantial improvement of coating density and adhesion. Using recently introduced pulse magnetron sputtering technology allows further increases in the ionization rate, but the drawback of this approach is the reduction in the coating deposition rate (productivity). Large pulses can also generate an increased amount of macroparticles increasing the density of surface defects. PACVD, magnetron sputtering and EBPVD processes produce vapor plasma flow with low, near thermal kinetic energy, which can be detrimental for deposition of coating on substrates composed of materials with low electrical conductivity.

The cathodic arc deposition (CAD) technology can evaporate electrically conductive (metal like) targets and produce a nearly 100% ionized vapor plasma with kinetic energy of ions ranging from 40 to 200 eV and it does not require sputtering gas, but it suffers from large amount of macroparticles generated along with vapor plasma from cathode arc spots located at the cathode target surface. This setback of the conventional CAD technology is overcome by filtered cathodic arc processes, which effectively eliminate the macroparticles and yield up to 100% ionized and atomized metal vapor flow. This filtration can occur by means of mechanical shutters in the direct path of the plasma to the substrate materials. The filtration can also be accomplished by bending the plasma flow in one or more bends using magnetic steering coils. In the following a brief and simplified description of this technology will be provided, however, it should be understood that this is given merely to allow clarification of the process parameters and is not intended as an accurate scientific description of the mechanisms involved in filtered cathodic arc technology. In cathodic arc technology metal droplets and metal vapour are generated by applying an arc of high current to a negatively charged target metal in a vacuum chamber. At the same time, high concentrations of electrons are also released from the target metal cathode at high speed. The vacuum chamber, by definition, contains a gas at a low pressure, and it is usual that the gas is fed to the chamber as plasma containing a gas or a gas mixture at high temperature in a partially ionized state. The high speed electrons collide with the gas molecules, thereby further ionizing the gas molecules, which in turn collide with and ionize the metal droplets and metal vapour. The ionized gas and the ionized metal vapor and metal droplets proceed towards the negatively charged substrate also located in the vacuum chamber. The metal deposits in a layer over the surface of the substrate. When the gas is an inert gas no reaction takes place between the ionized gas and metal vapour. On the other hand, in the instance of the plasma also containing reactive gases, the ionized gases will react with the metal vapour, forming a deposited ceramic compound layer. In conventional cathodic arc plasma deposition the vaporized metal droplets in the plasma can vary in size, thus the metal or the ceramic compound deposited on the substrate is likely to exhibit widely varying grain sizes and surface unevenness.

In a recent modification of plasma technology deposits are obtained by filtering a cathodic arc source by means of appropriately adjusted magnetic fields. An example of such a cathodic arc plasma coating apparatus is described in U.S. Pat. No. 5,435,900 issued to V. I. Gorokhovsky, which is incorporated herein by reference. The operating pressure of the filtered arc deposition process ranges from $10^{-6}$ torr to $10^{-2}$ torr, which overlaps with most of the conventional plasma assisted PVD and low pressure CVD processes. This makes it possible to use the filtered arc plasma environment as ionization and activation means for hybrid processes utilizing a combination of different conventional PVD and low pressure CVD processes operating in a filtered arc plasma immersion environment as it is better described in US Pat. Application Publication No. 2004/0168637 A1 of V. I. Gorokhovsky, which is incorporated herein by reference. The hybrid surface engineering system, based on this approach, which includes conventional unbalanced magnetron sputtering plasma sources, EBPVD evaporation sources, thermal evaporation source, low pressure PACVD plasma source and large area dual filtered arc depositing (LAFAD) plasma sources, which can be used in practicing the present invention is shown schematically in FIG. 1. The arc depositing apparatus 10, contains a main vacuum chamber 6, housing a substrate platform 1, bearing double or triple rotating satellites 8, which are utilized in supporting substrates providing appropriate depositing surfaces. Substrate platform 1 is connected to a negative bias voltage power supply for rendering the substrate surfaces receptive of ions during the deposition process. Two plasma guide chambers 2 and 2' are located on opposing sides of vacuum chamber 6, each enclosing two large area dual filtered cathodic arc sources 3, attached to the flanges within the plasma guide chamber. Thus the vacuum chamber 6 contains altogether four cathodic arc sources 3, but only one of those is described in detail. In the preferred arrangement two cathodic arc sources 3 are utilized, located at opposing flanged ends of the plasma guide chamber 2, each having a metal target electrode 4. The metal target 4, is connected to the negative pole of a low voltage high current power supply, thus being capable of generating separate metal vapour jets which converge into metal plasma stream 11. The metal vapour jets are focused and steered by magnetic coils 12 and 13. Deflecting coils 9 bend and collimate plasma streams 11 to direct the flow towards the substrate depositing surfaces. Metal droplets of larger size, and most of the non-ionized neutral species are trapped on [the] baffles 5, of anode-separators 17. Anode-separators 17, bear[s] a positive potential relative to the plasma stream and thus repel[s] the positively charged ions, urging such ions towards the substrates. Vacuum chamber 6, is equipped with a front door 16, for loading the substrates to be coated. Front door 16, also has view ports and flanges 7, for diagnostic assessment and control of the deposition process. On the perimeter of the vacuum chamber, preferably opposite front door 16, is located vacuum pumping system 15, which is not shown in detail. The vacuum chamber 6, also has gas entry ports (not shown), two unbalanced magnetrons 18 and 18' equipped with $B_4C$ targets, two electron beam evaporators 19 and 19' and a thermal evaporator 20. When the deflecting coils are not activated, the cathodic targets 4, serve as powerful electron emitters, thereby providing high electron currents between the cathodic targets and auxiliary anodes 14. This arrangement creates a highly ionized gaseous environment during all stages of the process: ion cleaning, ion nitriding and deposition of coating layers. In addition, some form of heaters can be connected to the auxiliary anodes 14, to allow the temperature of the depositing surface of the substrate to be controlled independently. Metal vapor plasma flow can be effectively interrupted by using the LAFAD deflecting magnetic field as a magnetic shutter. In a pulse filtering mode magnetic deflecting coils are periodically turning on and off. This allows creating a multilayer and/or modulated coating composition with a wide range of the sizes of sublayers.

Figure 2A:
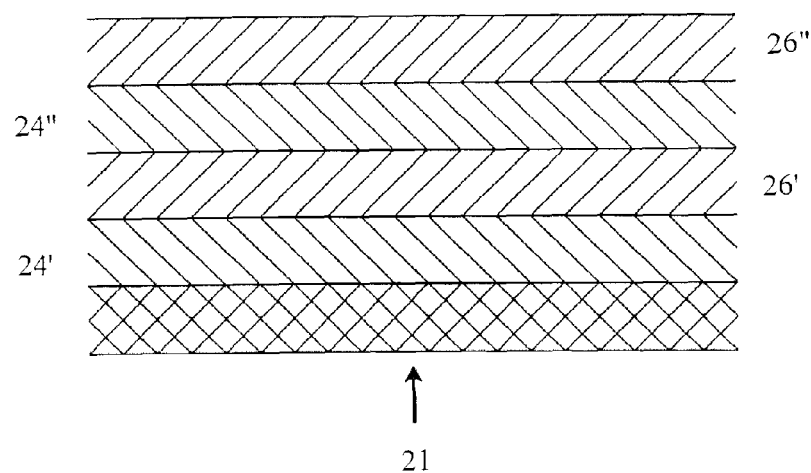
FIG. 2 is schematic illustration of coating composition modulation: a—multilayer Me/MeN coating architecture; b—modulated coating architecture.

FIG. 2a shows the multilayer coating architecture consisting of metal sublayers in turn with ceramic sublayers similar to that of the prior art described in U.S. Pat. No. 6,617,057 issued to V. I. Gorokhovsky, which is incorporated herein by reference. The multilayer bondcoating is shown schematically in FIG. 2a. by reference numeral 21. The steel substrate surface which can have been optionally treated by ion nitriding or oxynitriding, is represented as the bottom section 22. The exemplified coating comprises two metal-ceramic layer pairs. The first metal layer, such as titanium, of the first metal-ceramic pair is shown as 24' and the third layer, which is of the same metal in the second pair, is represented as 24". The second layer which is a ceramic layer, such as for example, titanium carbide, in the first pair is represented by reference numeral 26' and the fourth layer which is of the same composition as the ceramic layer of the first pair, is shown as 26". This coating architecture can be further improved by reducing the bilayer periods to nanometric size, incorporating nanocomposite cermet structure into the ceramic sublayers and modulating the content of selected elements across the coating. One of the ways of making the laminated coating architecture is by modulating the current of one of the primary cathodic arc sources of the LAFAD plasma source resulting in a modulating content of selected elements throughout the coating.

Figure 2B:
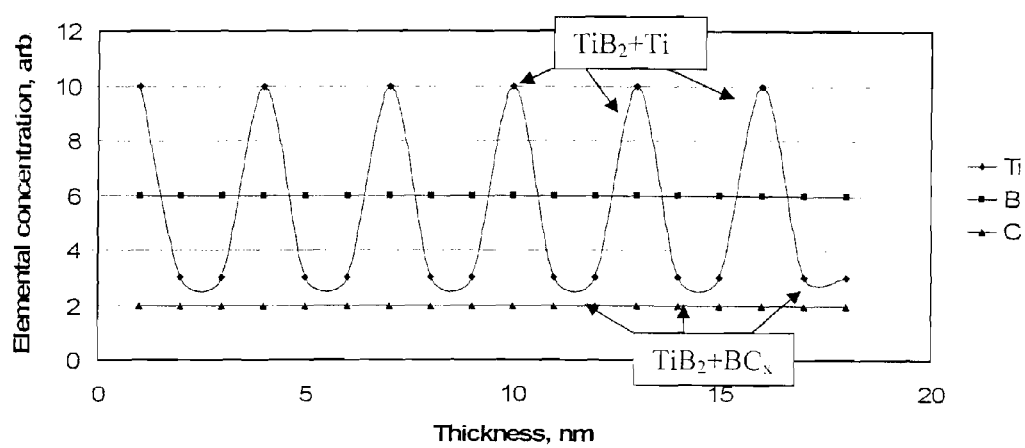

FIG. 2b shows an example of a TiBC coating with a modulated titanium content, which is deposited by surface engineering system presented in FIG. 1 with a dual filtered arc LAFAD plasma source having two primary cathodic arc sources equipped with titanium evaporating targets and two unbalanced magnetrons equipped with $B_4C$ sputtering targets. The modulation of Ti content is achieved by magnetic shuttering of LAFAD source by periodically turning ON and OFF the magnetic deflecting coils. Additionally, this mode can be used for precise thermal management of the substrate in plasma vapor deposition process as it will be in more details described below. It is noted, however, that the apparatus of FIG. 1 is merely an example of a device utilizing magnetic plasma arc filtering. Any other high temperature vapour depositing apparatus which may and may not be fitted with magnetic plasma arc filtering means can be employed in practicing the present invention. The operation pressure of the LAFAD plasma source which ranges from $10^{-6}$ torr to $10^{-2}$ torr overlaps with almost all conventional low pressure PVD and PACVD plasma sources. This allows a wide variety of coating architectures and compositions to be deposited using evaporation targets composed of different materials as well as different reaction gas precursors in a strongly ionized plasma environment. It is also noted, that the preferred vapour depositing surface engineering system shown in FIG. 1 contains an arrangement with four selected cathodic targets, two magnetron targets, two EBPVD evaporation crucibles and resistive evaporation boat however, it is possible to operate the device with only two cathodic targets and/or only one magnetron target and/or only one EBPVD crucible and/or only one resistive evaporation boat.

The application of magnetic filtering of the cathodic arc stream eliminates macroparticles, as well as neutral non-ionized species, and thereby substantially only ionized metal vapor and nano-sized metal droplets carrying a charge, will reach the substrate. This results in deposit layers of even grain size, and surfaces having very low micro-roughness. Such surfaces can be referred to as evenly deposited surfaces.

The substrate selected for deposition in the present process is a conductive material, such as a metal or a hard-wearing substance having relatively high electrical conductivity. It can be chosen from different grades of stainless steels or titanium alloys. In one of the preferred embodiments the substrate is stainless steel of the AISI 300, 400 (such as high chromium 440A, 440B, 440C and 440XH (Carpenter) stainless steel) or 1700 series, such as the 17-4 series. One skilled in the recognizes the compositions of several of these preferred steels, for example; TRIM RITE-C 0.15/0.30, Mn 1.00, P 0.04, S 0.03, Si 1.00, Cr 13.50/15.00, Ni 0.25/1.00, Mo 0.04/1.00, balance Fe; 440E-Se—C 0.95/1.20, Mn 1.25, P 0.040, S or Se 0.15 (min.), Si 1.00, Cr 16.00/18.00, Mo 0.60, balance Fe; TRINAMET-type analysis C (max.) 0.30%, Mn (max.) 1.00%, P (max.) 0.040%, S (max.) 0.03%, Si (max.) 1.00%, Cr 12.00 to 14.00%, Mo 1.00 to 3.00%, Cu 2.00 to 3.00%, Fe, balance; IRK91 (see U.S. Patent Application Publication No. 2004/0197581) (Sandvik Bioline)-C+N≤0.05, Cr 12.0, Ni 9.0, Mo 4.0, Ti 0.9, Al 0.30, Si 0.15, Cu 2.0; 7C27Mo2-C 0.38, Si 0.4, Mn 0.6, P (max.) 0.025, S (max.) 0.01, Cr 13.5, Mo 1.0; 20AP-C 1.0, Si 0.2, Mn 0.4, P (max.) 0.03, S 0.05, Cr (max.) 0.10, Ni (max.) 0.10, Mo (max.) 0.03, other Pb 0.2. In another embodiments it is a shape memory alloy such as NITINOL, ENDONOL, or NiTi alloy composed of various compositions of nickel and titanium or equiatomic (50/50 at. %) composition of Nickel and Titanium. It is possible that NiTi steels be doped with other elements as well, such as, for example, copper.

The coatings and methods of the subject invention are exemplified for use primarily on endofiles and implant drills. The subject coatings and methods can be applied to scalers, ultrasonic scalers, and dental burs as well. In preferred embodiments, scalers are made of the following steels: 440A, 440C, 440Xh, 440F—Se, 1RK91, 13C26, 4C27Mo2, and 20AP. Both Piezo and magnetostrictive ultrasonic scalers are preferably made of: the 17-4 family of steels, 13-8, TRIM-RITE, TTRINAMET, 420, 1RK91, 13C26, 4C27Mo2, 20 AP. Preferred compositions for implant drills include: 17-4 steel and 300 series steel, 1RK91, 13C26, 4C27Mo2, and 20AP. Dental burs are preferably carbide-stainless steel with high hardness. It is preferred that endofiles are made of 17-4, 13-8, NiTi, TRIMRITE, TRINAMET 420, 1RK91, 13C26, 4C27Mo2, and 20 AP steels.

The substrate surface to be coated is first cleaned, by a usual cleaning processes which can include degreasing, tumbling, grinding, polishing, chemical cleaning, degreasing, electrolytic cleaning, ion bombardment or similar conventional cleaning steps which can render the surface receptive of the deposited substance.

The cleaned substrate can optionally be ion nitrided, oxi-nitrided or carburised or subjected to ion implantation to increase the hardness and corrosion resistance of the substrate surface and possibly further improve adherence of the deposited coating. The ion nitriding or ion implantation step may be conducted in a separate apparatus, or the universal surface engineering system shown on FIG. 1 can be adapted to the ion nitriding or ion implantation process step. This treatment creates a case on the surface of the substrate to be coated preventing against the egg-shell effect which can reduce performance of thin film hard coating deposited on relatively soft substrate. This case is designed to accommodate the plastic deformation of relatively soft substrate.

The substrate having a cleaned, and optionally nitrided depositing surface, is then placed in the vacuum chamber of a suitable cathode arc plasma depositing device having at least one of plasma vapor deposition means, such as described above. The arc cathode targets, magnetron targets, EBPVD evaporating material, resistive evaporating material and PACVD reactive gaseous precursors are selected for the plasma vapour generation, are selected as they are capable of forming low friction, anti-galling, hard, wear and corrosion resistant compounds by vapour deposition. The metallic and non-metallic elements which are preferred in such compound formation are titanium, chromium, vanadium, molybdenum, aluminum, hafnium, zirconium, niobium, tungsten, their alloys, carbon, boron, silicon, and elements of similar nature. The preferred reaction gaseous precursors are nitrogen, hydrogen, oxygen, hydro-carbon gases, borazin, boron trichloride, trimethylsilane (3MS) and gases of similar nature.

The gas atmosphere in the cathodic arc depositing device is controlled such that it can yield either a vapour deposited metal layer or a vapour deposited ceramic compound layer. The ceramic compounds that have desired wear resistance, corrosion resistance and hardness are the carbides, nitrides, carbonitrides, oxycarbides and oxynitrides of the above listed metals. The plasma for depositing the desired ceramic layers contains one or more of the following gases: nitrogen, methane or other hydro-carbon gas, borazin, 3MS and oxygen. In the vapour deposition of layers of the above listed metals only argon, or similar inert gas containing plasma is used. Argon may also be utilized to dilute or carry the gases reacting with the metal vapour or metal deposit, to form the desired ceramic [metal] compounds. The metal and ceramic compound combinations suitable for forming hard, wear resistant coatings by vapour deposition in the present invention, are listed in Table 1 below.

The first metal layer to form a metal-ceramic compound layer pair, is obtained by having one of the metals listed above as cathodic target metal. The metal layer is deposited in an inert gas, usually argon, in a thickness ranging between 0.01 µm and 0.2 µm. The preferred range is 0.01 to 0.1 µm. Usually, the same cathodic target metal is used in obtaining the second, ceramic compound layer of the pair, however, the cathodic plasma arc composition is adjusted to contain the gaseous component required to form the appropriate ceramic [metal] compound. The thickness of the vapour deposited ceramic compound layer is usually selected to be between 0.01 and 2 µm, depending on the design, shape and ultimate purpose of the deposited coating on the substrate. The metal/ceramic multilayer coating has to have a high cohesion toughness, which is often determined by resistance to plastic deformation parameter $H^3/E^{*2}$, where H is hardness and E is elastic modulus of the coating. It is required that multilayer coating of this invention has the $H^3/E^{*2}>0.05$.

The multilayer cermet coatings using a ceramic sublayers composed of nitride, carbonitride, carbide, boride, carboboride, carbo-boron-nitrides and combinations thereof can be used as a coating protecting against abrasion wear and corrosion as described in U.S. Pat. No. 6,617,057 issued to V. I. Gorokhovsky, which is incorporated herein by reference. FIG. 3 shows the rotary instrument blade 28 having two sides with multilayer cermet coating 30. Table 1 lists the preferred metals and alloys used for cathodic targets to obtain the metal layer, and the appropriate layer of ceramic compounds in conjunction with the metal layer. It is to be noted, however, that in some instances, it is preferred to use two separate metal targets as cathodes, operated simultaneously, to obtain the deposited metal alloy layer. For example, it may be convenient to use an aluminum target metal cathode and a titanium target metal cathode operated simultaneously, to obtain an Al—Ti alloy layer.

Figure 4:
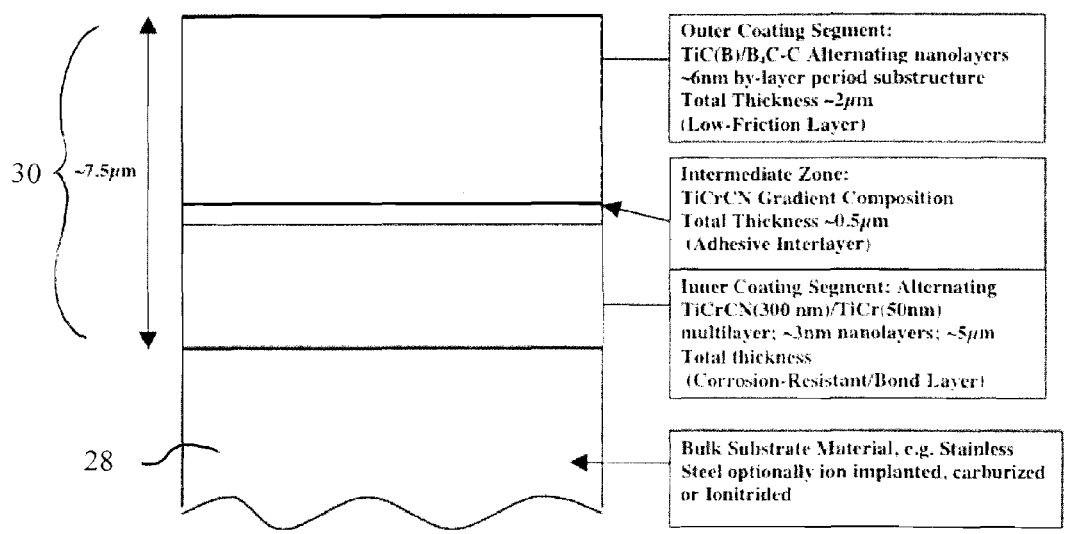
FIG. 4 is a schematic drawing of a functionally graded coating architecture.

While the multilayer metal-ceramic coating architecture addresses the abrasion wear resistance and corrosion resistance, there are important issues which must be addressed in the case of rotary dental instruments such as implant drills and root canal endofiles. In this case the friction and stickiness between the instrument surface and counterpart (body tissue) creates a large torsional momentum which contributes to the development of cracks through the surface of the tool and leads to separation of the instrument. As shown in the U.S. Pat. No. 6,074,209 issued to W. B. Johnson, which is incorporated herein by reference, torsional fatigue is the main reason for the failure of rotary endodontic instruments such as endofiles. When debris sticks to the surface of the rotary instrument flute it prevents the flute from removing the debris from the hole, accumulates a large amount of debris along the flute and dramatically increases the torsional momentum imposed on the tool. In addition to reduction of friction and stickiness the top coating of the subject invention imposes a substantial compressive stress on the surface layer of the instrument, which prevents cracks from developing and slows the propagation of the cracks effectively improving the torsional fatigue life of the instrument. The top coating of this invention typically provides the compressive stress ranging from 0.1 to 8 GPa. The bottom multilayer metal-ceramic coating segment protects against both pitting and stress induced corrosion. The integrity of this segment is quite important. If the metal surface finish is near perfect the pitting and stress corrosion is concentrated through the coating defects, imperfections, voids, porosity. The LAFAD technology substantially reduces the surface defects by effectively eliminating the macroparticles and increasing ionization of the depositing metal-gaseous plasma. Using intense ion bombardment during vapor plasma deposition process allows not only reduction of the coating roughness, but also fills and mitigates the initial surface defects via the increase of adatom mobility and surface diffusivity. FIG. 4 shows the preferred embodiment of the coating design shown in FIG. 3 which employs the functionally graded coating architecture having multilayer Me/MeN based bottom portion (Me means a metallic component which can be chosen from the metals presented in Table 1) followed by transition carbonitride interlayer and topped with carbide single layer or multilayer coating, having an excessive amount of free amorphous carbon.

Figure 5:
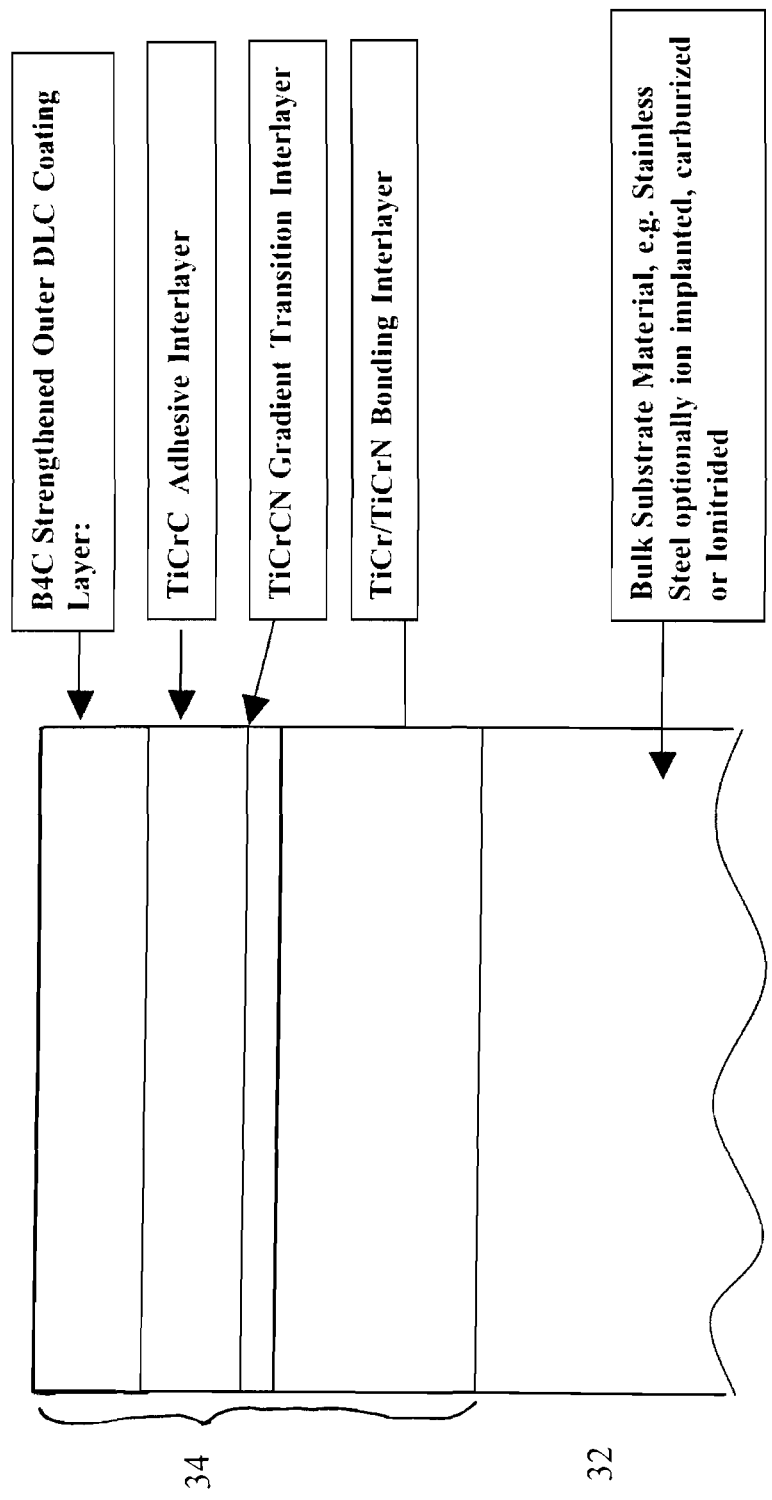
FIG. 5 is a schematic drawing of the low friction, anti-galling architecture including $B_4C$ strengthened diamond-like coating with a bondcoating interlayer.

FIG. 5 shows a blade 32 having a single or multilayer low friction anti-galling diamond-like coating composed of a mixture of diamond and graphite bonded atoms. The hydrogen and/or nitrogen can be optionally added to this matrix composition to further improve coating toughness and wear resistance. In a preferred embodiment the diamond-like carbon matrix is doped by boron, silicon and/or transition metals such as Ti, Al, V, Cr, Mo to form nanocrystalline phases embedded in the carbon diamond-like matrix. The size of nanocrystals ranges from 0.5 to 100 nm. The suitable Me/MeC or Me/MeN/MeCN/MeC bond coating is deposited between DLC layer and substrate to secure adhesion of the DLC low friction anti-galling layer to metal substrate.

Figure 6A:
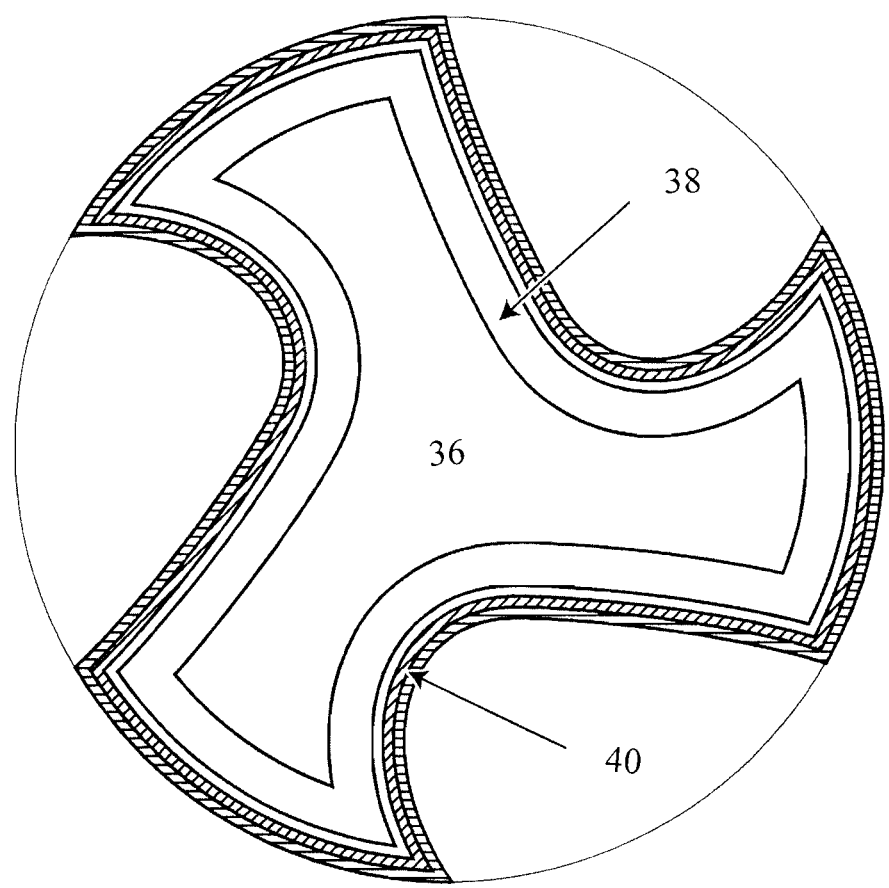
FIG. 6a is a schematic drawing of an endofile with a duplex ionitriding+multilayer coating treatment.

FIG. 6a shows the implant drill 36, made of 300 series stainless steel having a duplex treatment: bottom ionitrided case 38 having thickness of about 5 μm followed by top multilayer Ti/TiN coating 42 having thickness of about 1 μm. This coating is deposited in LAFAD surface engineering system shown in FIG. 1. Prior to loading in the LAFAD chamber the substrates are subjected to grinding to make a flute followed by mild vibratory tumbling to remove any type of deburrs and defective surface layer. The drills are loaded on double rotating satellites of the rotating substrate table of the LAFAD chamber. At the beginning of the deposition process the substrates are heated by means of radiation to 300° C. After that ion cleaning is conducted in argon auxiliary arc discharge plasma at 0.5 mTorr and 250 volts bias. The auxiliary arc discharge is generated between the primary cathodic arc targets (titanium) of the LAFAD-1 plasma source and auxiliary anode plate installed at the back of the LAFAD chamber (FIG. 1) when deflecting field of the filtered arc source is OFF. After 10 min of ion cleaning the plasma creating gas is changed to nitrogen and auxiliary arc plasma immersion ionitriding process is employed for 10 min to create a thin ionitrided case. After that stage the deflecting magnetic field is turn ON, the pressure is reduced to 0.3 mTorr, the DC pulse bias voltage is reduced to 40 volts and multilayer Ti/TiN is deposited for 120 min. During the coating deposition stage argon is used for 3 min for deposition of the Ti sublayer and nitrogen is used for 7 min for deposition of the TiN sublayer of Ti/TiN multilayer cermet coating. Typical deposition rate of Ti based coating by LAFAD plasma source with double rotation is 0.8 μm/hr for Ti metallic sublayer and 0.4 μm/hr for TiN ceramic sublayer layer. This results in a thickness of Ti sublayer in this process of about 30 nm and thickness of TiN sublayer of about 70 nm. The total thickness of the coating deposited in this process is about 1.2 μm.

Figure 6B:
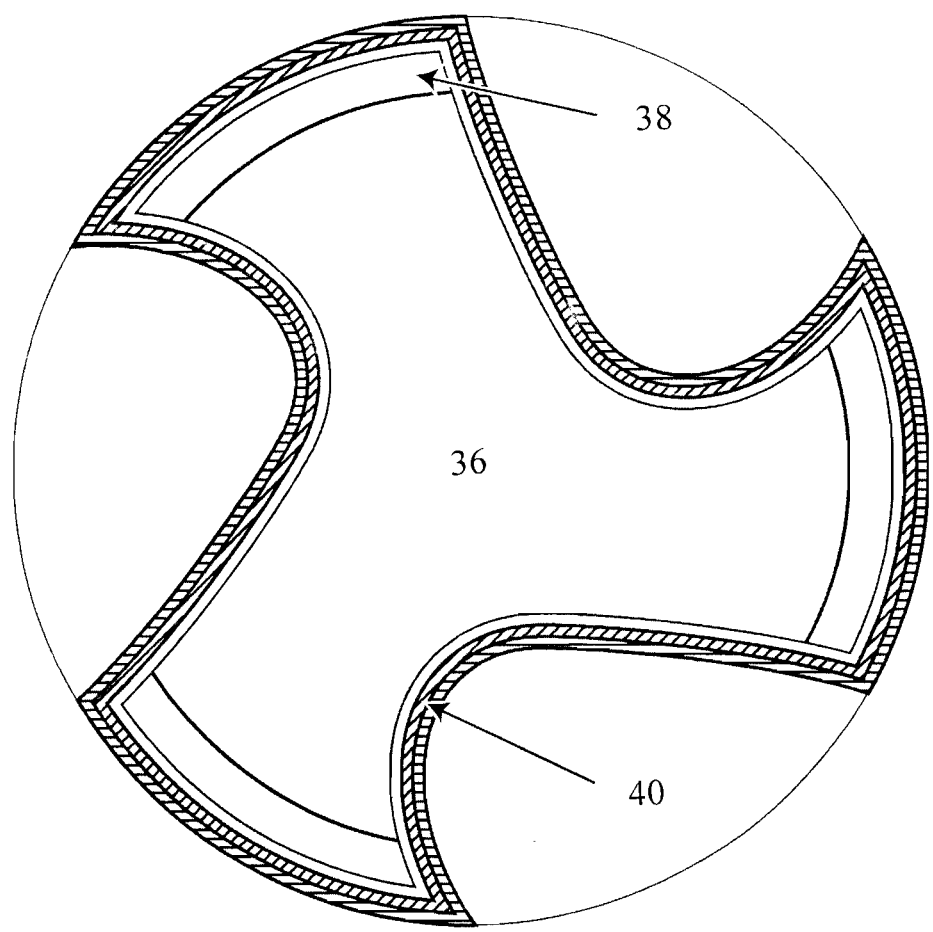
FIG. 6b is a schematic drawing of an endofile with a duplex coatings similar to that shown in FIG. 6a, but with an ionitrided layer only on the face side and a multilayer coating on both sides of the flute.

FIG. 6b shows the implant drill 36 of FIG. 6a having a face side of the flute ionitrided with ionitrided layer 38 having a thickness of about 5 μm and a multilayer titanium nitride 40, having a thickness of about 2 μm, overlaying the entire flute. Said ionitrided layer and titanium nitride layer overlap in the vicinity of the very edge of the cutter. In this fabrication process the drills are subjected to the same procedures as that of the previously described regarding FIG. 6a, but at first the drills are not ground and do not have a flute. After the ionitriding stage is completed the drill blanks are cooled, removed from the vacuum chamber and subjected to grinding to fabricate the flute. After that the drills are vibratory tumbled for the short time and loaded in the LAFAD chamber for deposition of Ti/TiN multilayer coating as it is previously described. As a result the duplex ionitriding/(Ti/TiN) coating is deposited only on outer side of the flute, not affected by grinding while the inner side of the flute has only Ti/TiN multilayer coating deposited on steel substrate without an ionitrided case.

Figure 7A:
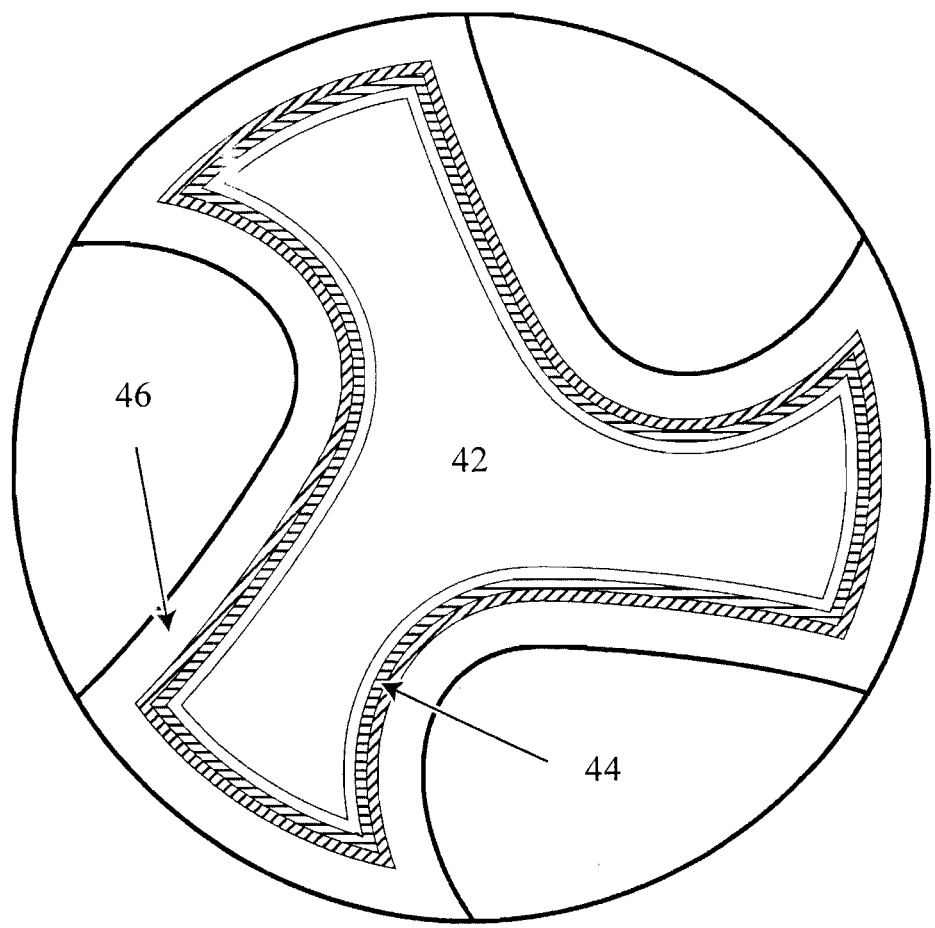
FIG. 7a is a schematic drawing of the cross-section of an endofile with a dual segment coating architecture including a first multilayer Me/MeN bondcoating segment and a nanocomposite low friction, anti-galling top coating segment.

FIG. 7a shows a cross-section of endofile 42 coated with a preferred embodiment of the coating of the subject invention. In this embodiment, the endofile 42 is made of 17-4 stainless steel. The bottom bond coating segment 44 is made of multilayer gradient cermet Me/MeN/MeCN/MeC, where Me element can be taken from transition metals such as Ti, V, Cr, Zr, Al or their combinations (i.e. TiCr, TiZr, TiAl, CrAl, TiV etc.) coating having a thickness of about 100 nm which is followed by low friction top segment 46 $B_4C$ added carbon DLC layer having thickness of about 250 nm. The bottom segment coating is deposited by LAFAD plasma source with appropriate primary cathodic arc targets (titanium in case of titanium based cermet coating) in a process similar to that of previously discussed with the following difference: after deposition of the Ti/TiN nitride multilayer coating portion of the bottom segment coating the methane is added gradually to the nitrogen plasma creating gas to deposit carbonitride sublayer. At the end of deposition of the Ti/TiN/TiCN portion of the bottom segment coating the nitrogen is completely replaced by methane for deposition of the carbide top portion of the bottom coating segment. Instead of methane the 3MS gas can be used resulting in TiSiCN/TiSiC composition. This composition consists of SiN amorphous matrix with inclusions of TiC and TiN nanocrystalline phases resulting in superhard properties of this layer. Adding the Si to the TiCN based composition can be also achieved by using TiSi alloy targets instead of pure titanium targets in primary cathodic arc sources of the LAFAD plasma source. After deposition of the bottom segment coating the deflection field of the LAFAD plasma source is turn OFF and the top coating segment is deposited by auxiliary arc plasma immersion magnetron sputtering process. In this process the plasma creating gas is argon with near 5% methane. The unbalanced magnetrons are turned ON and auxiliary arc discharge is established between primary cathode targets of the LAFAD source and auxiliary anode plate at the back of LAFAD chamber (FIG. 1). The targets of unbalanced magnetron are made of sintered $B_4C$ ceramic. The DC bias voltage is setup on −50 volts with 100 kHz repetition of pulse assistance frequency. The gas pressure is increased to 0.8-1 mTorr. Sputtering of the $B_4C$ targets in methane contained strongly ionized plasma immersion environment results in deposition of nanocomposite DLC layer doped with boron contained phases such as nanocrystalline boron carbide. The thickness of the top segment coating is about 1 μm.

Figure 7B:
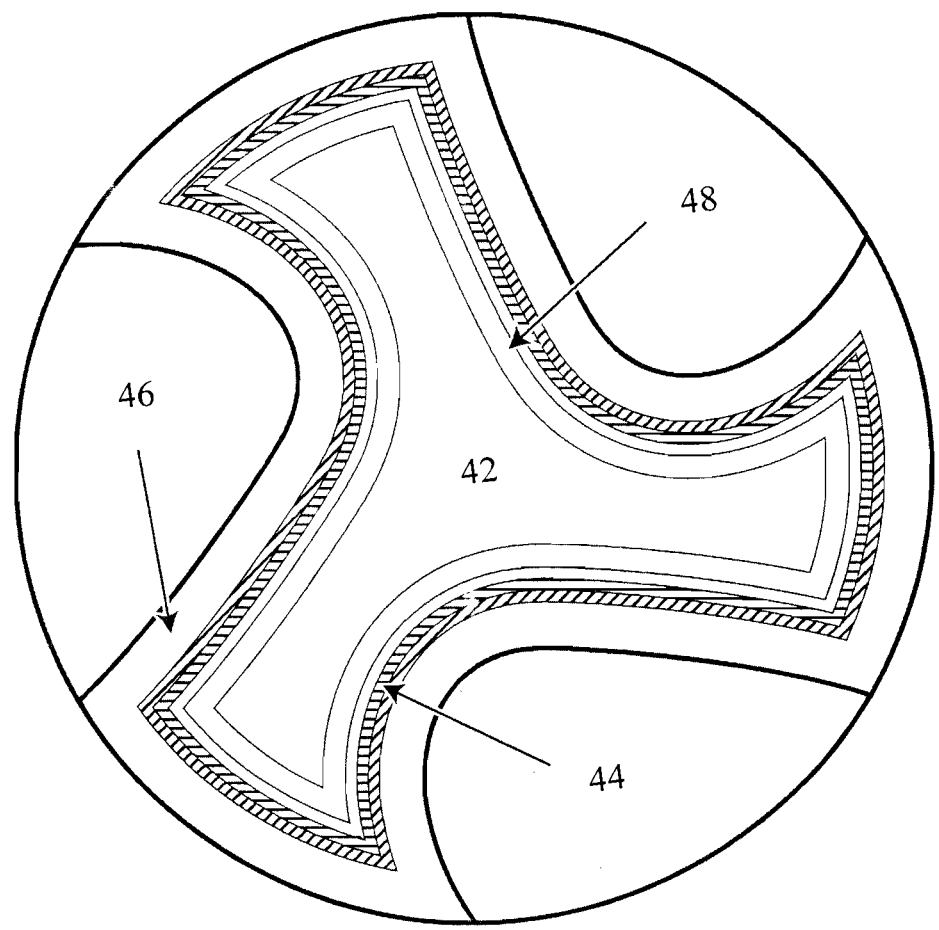
FIG. 7b is a schematic drawing of the cross-section of an endofile with a dual segment coating architecture similar to that shown in FIG. 7a, but with an ionitrided layer under the bond coating cermet layer.

FIG. 7b shows a cross section of a blade with a preferred embodiment of a triplex coatings. An ionitrided case 48 5 μm thick is followed by 2-segment coating 44, 46 similar to that shown in FIG. 7a. For deposition of this triplex coating architecture the ionitriding in auxiliary arc nitrogen plasma immersion environment is made before deposition of the Ti/TiN/TiCN/TiC bottom segment gradient multilayer coating as it is previously described.

Figure 8A:
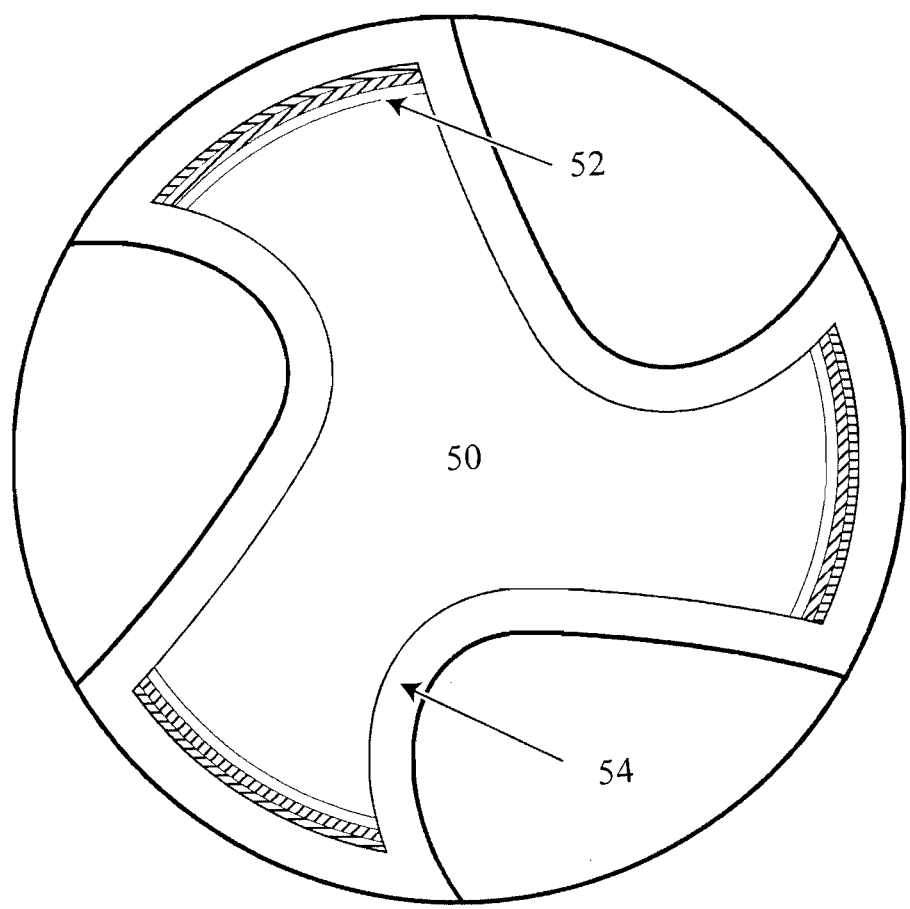
FIG. 8a is a schematic drawing of the cross-section of an endofile with the coating, having a bondcoating multilayer cermet bottom segment on the outer side of the flute and a low friction, $B_4C$ strengthened carbon DLC in the top segment overlaying the entire flute.

FIG. 8a shows a rotary dental endofile 50 coated with a preferred embodiment of the coating of the subject invention. In this embodiment, the endofile 50 is made of NITINOL or NiTi, the alloy is composed of a near 50/50 at. % of titanium and nickel components. It has a bottom bond segment coating 52 made of TiCr/TiCrN/TiCrCN/TiCrC multilayer and top anti-friction hydrogen free carbon DLC segment 54. It is achieved by deposition of DLC on a top of TiCrC bottom segment coating by LAFAD-2 filtered arc source equipped with graphite primary cathodic arc targets. During deposition of graphite coatings the substrates are setup up at floating potential and high voltage 2 kV pulses with width of 25 μs and repetition frequency of 600 Hz are provided to avoid overheating the tiny endofile substrates. The thickness of the bottom bond coating layer does not exceed 20 nm, while thickness of the top DLC segment is about 0.25 μm.

Figure 8B:
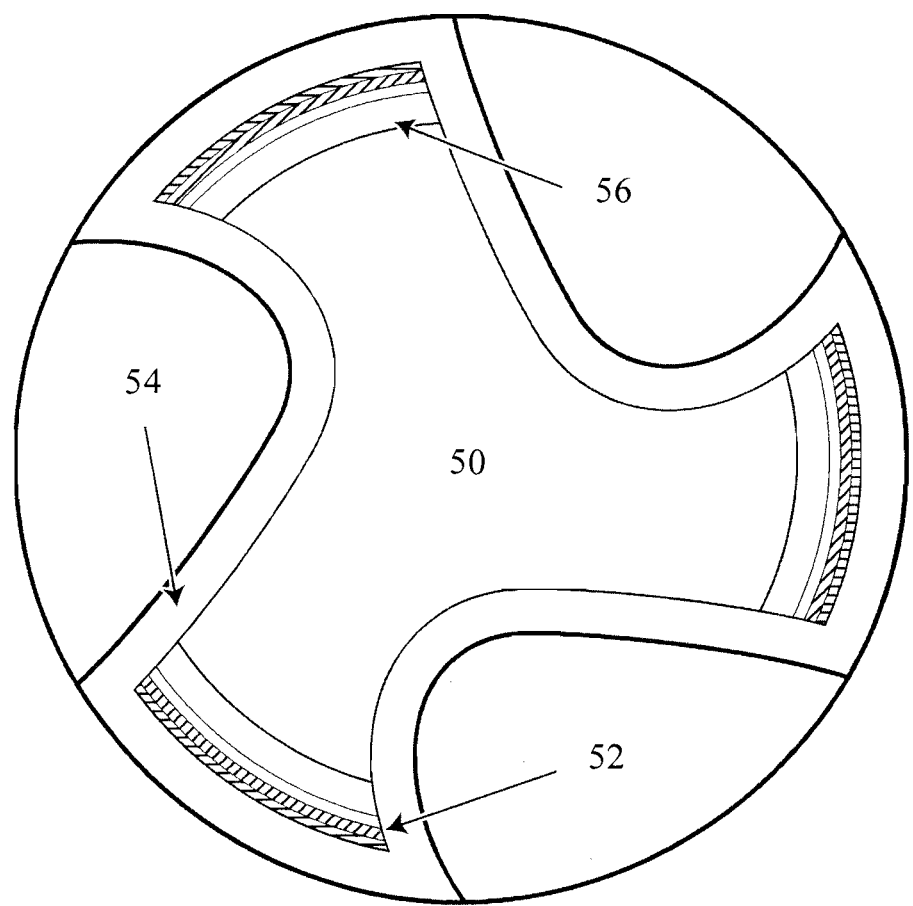
FIG. 8b is a schematic drawing of the cross-section of an endofile with the coating similar to that shown in FIG. 8a, but with the duplex bottom segment coating on the outer side of the flute.

FIG. 8b shows a blade 50 similar to the one shown in FIG. 8a but made of martensitic steel, having a cutting edge consisting of two opposite sides. The outer side is subjected to duplex treatment having ionitrided case 56 of about 5 μm thick followed by Ti/TiN/TiCN/TiC multilayer bond coating 52, having thickness of about 2-3 μm. The TiBCN nanocomposite low friction anti-galling coating 54 having thickness of about 0.5 μm is deposited on both sides of the blade overlaying both bottom segment bond coating 52 on outer side of the blade and uncoated steel surface 58 on inner side of the blade. To produce this coating architecture the blank blade (without the flute) was first subjected to ionitriding followed by TiN—TiCN—TiC multilayer gradient bottom cermet coating deposition process, than removed from the chamber and ground to create a flute, which leaves the inner side of the flute uncoated, while outer side of the flute (not ground) has duplex coating: 5 µm of ionitrided layer followed by 2 µm of the Ti/TiN/TiCN/TiC coating layer. Than the substrate is cleaned by mild vibratory tumbling and loaded in the LAFAD chamber for the final top segment coating deposited by filtered arc plasma immersion magnetron sputtering process of B4C doped DLC coating discussed in a previous paragraph. The resulting B4C+DLC top coating segment having a thickness of about 0.5 µm overlaps both duplex coated outer side of the flute and uncoated inner side of the flute.

FIG. 8c shows a blade 50 made of martensitic steel, having a cutting edge consisting of two opposite sides. In this case the outer side of the blade has a 2-segment coating consisting of the bottom Ti/TiN/TiCN/TiC multilayer bond coating 52, having thickness of about 2-3 µm followed by top TiBCN low friction anti-galling coating having thickness of about 0.5 µm. The inner side of the blade has duplex coating consisting of an ionitrided layer 56 having thickness of about 5 µm followed by a TiBCN coating segment. The ionitrided layer overlaps the titanium nitride bottom segment coating layer on the very edge of the cutter. The TiBCN nanocomposite low friction anti-galling coating 54 having thickness of about 0.5 µm is deposited on both side of the blade overlaying both TiN bottom segment coating on outer side of the blade and ionitrided steel surface on inner side of the blade. To produce this coating architecture the blade is first subjected to the bottom cermet coating deposition process, than subsequently removed from the chamber and grinded to create a flute, which leaves the inner side of the flute uncoated, while outer side of the flute (not subjected to grinding) has 2 µm of the Ti/TiN/TiCN/TiC coating. After this stage the substrate may be subjected to heat treatment to restore the maximum hardness of the core metal. After that the substrate is cleaned by mild vibratory tumbling and loaded in the LAFAD chamber for the second subsequent coating process. At this time the blade is first ionitrided to create ionitrided layers on the sides of the blade not covered by TiN coating (the coating was removed during grinding of this side of the flute) followed by deposition of B$_4$C doped DLC coating by plasma immersion magnetron sputtering process discussed in a previous paragraph. The TiN based coating on the outer side of the flute effectively prevents the diffusion of nitrogen into steel because of its outstanding diffusion barrier properties. In this coating architecture the DLC top coating segment is overlaying TiN—TiCN—TiC bond coating on the outer side of the blade and the ionitrided case on inner side of the blade.

Figure 10A:
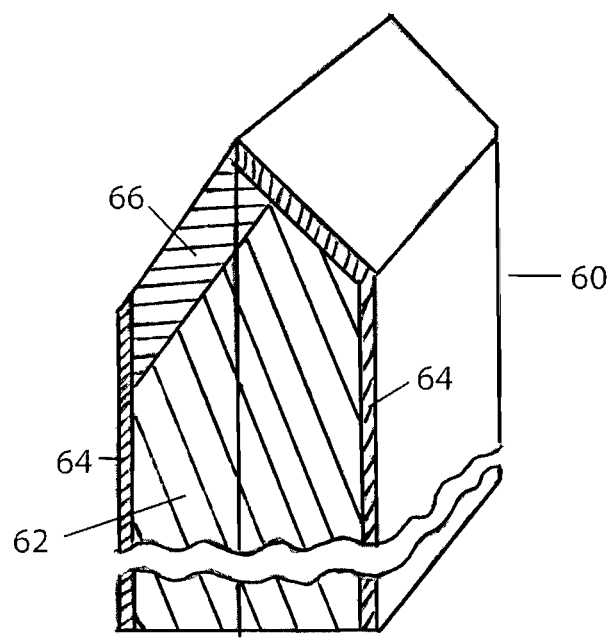
FIG. 10 is a schematic drawing of the different cross sections (a-c) of the blade with a duplex coating on one side and a cermet coating on the opposite side of the cutting edge.
Figure 10B:
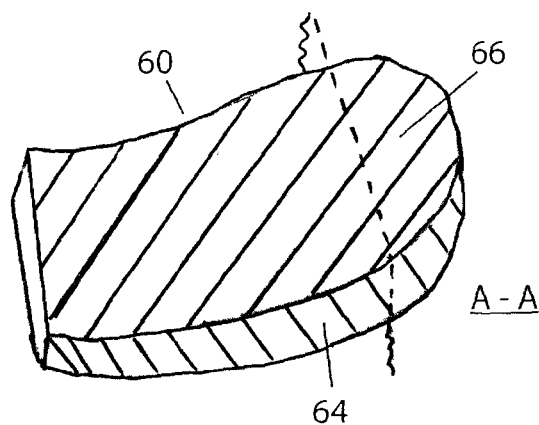
Figure 10C:
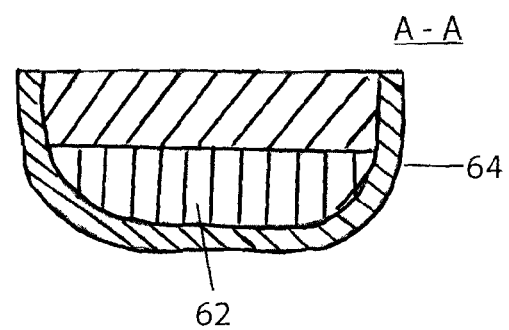
Figure 11A:
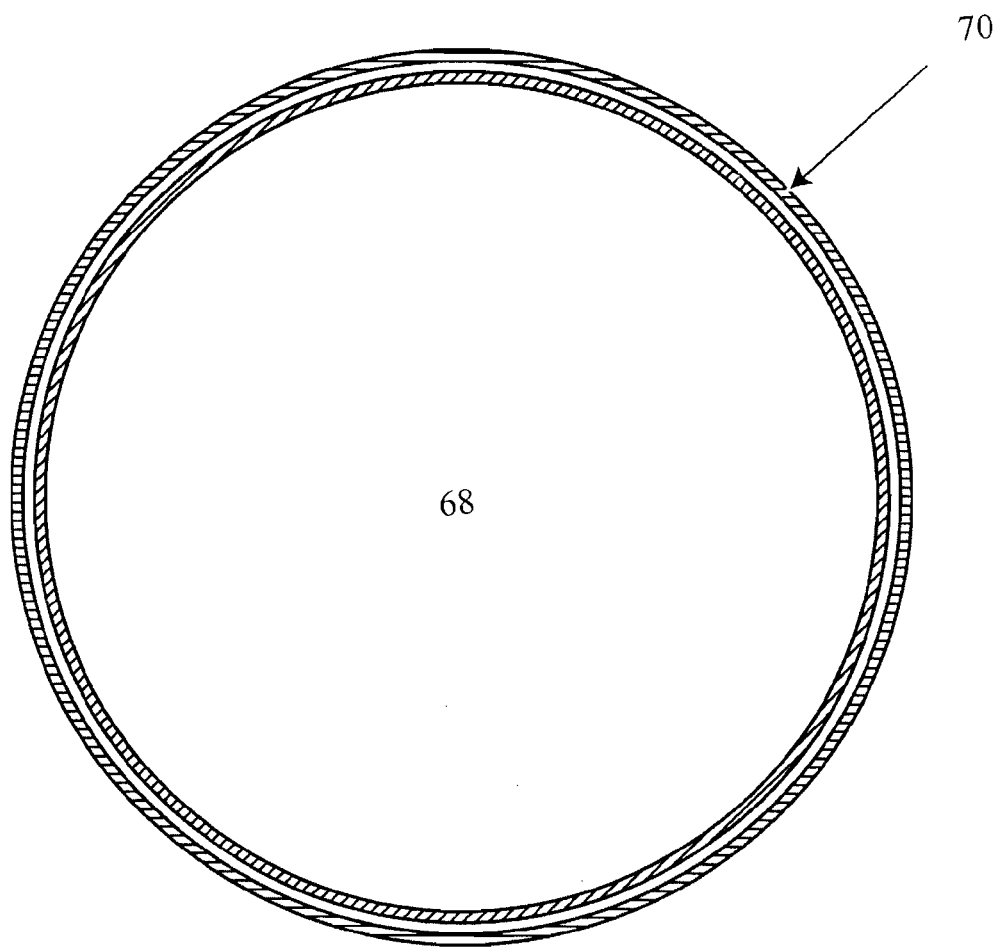
FIG. 11 shows a schematic drawings of cross-sections of the rotary dental instrument throughout all stages of its fabrication (a-d).
Figure 11B:
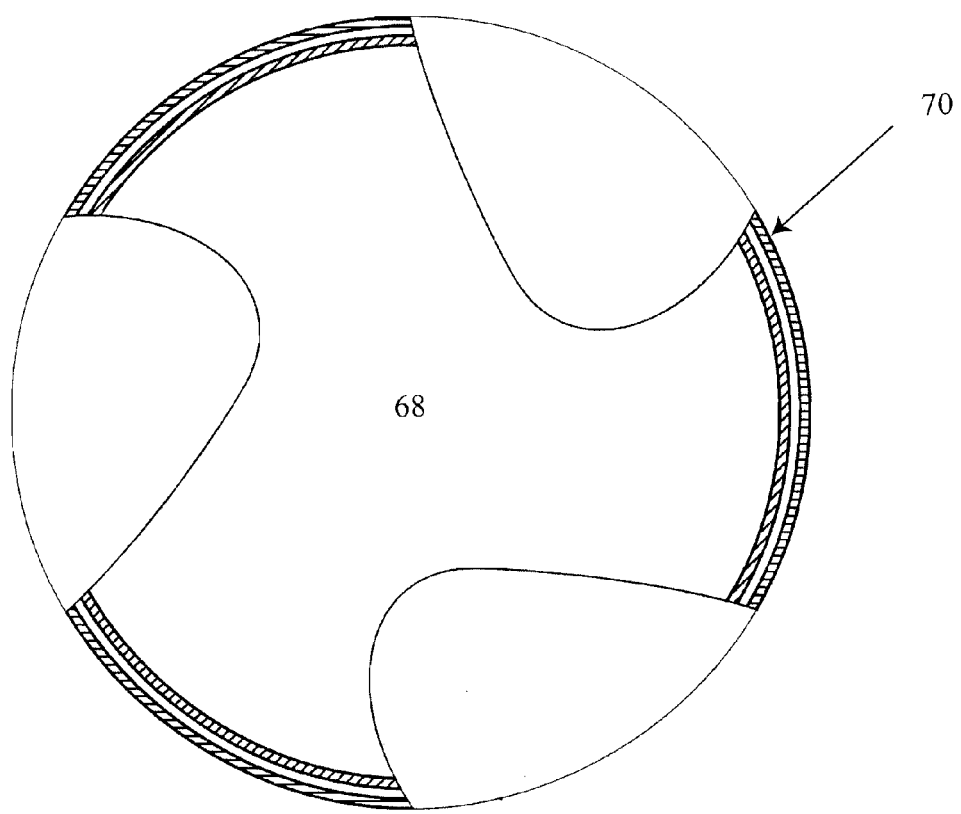
Figure 11C:
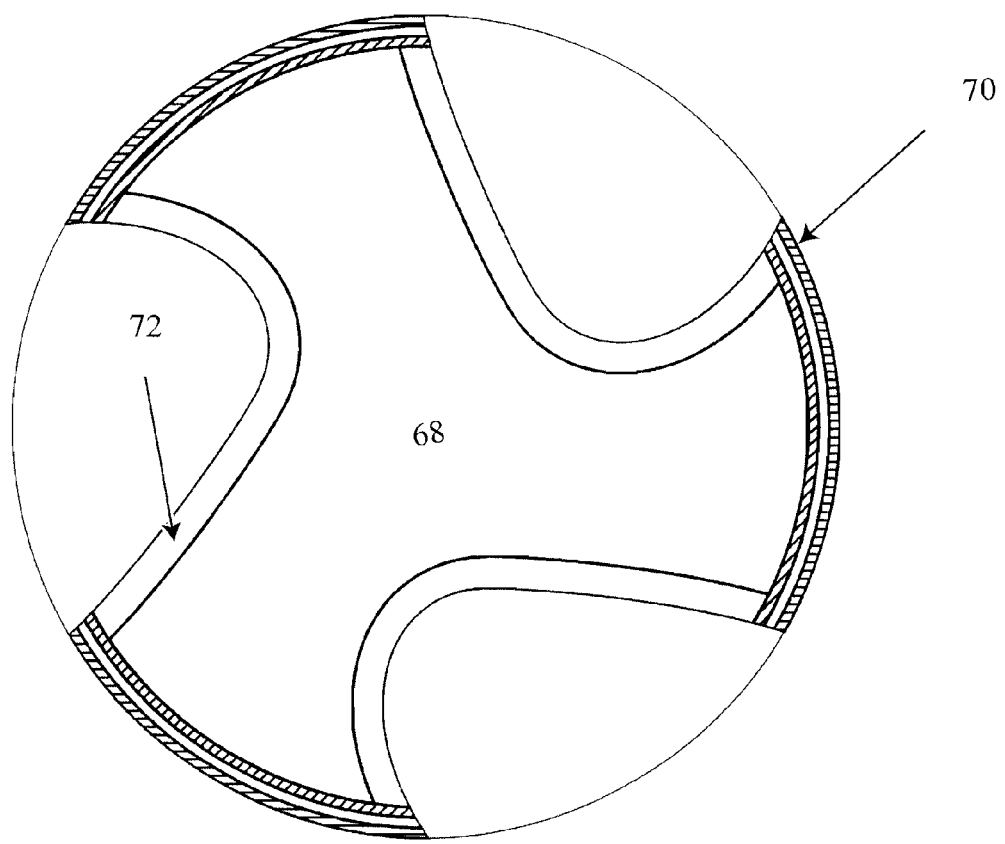
Figure 11D:
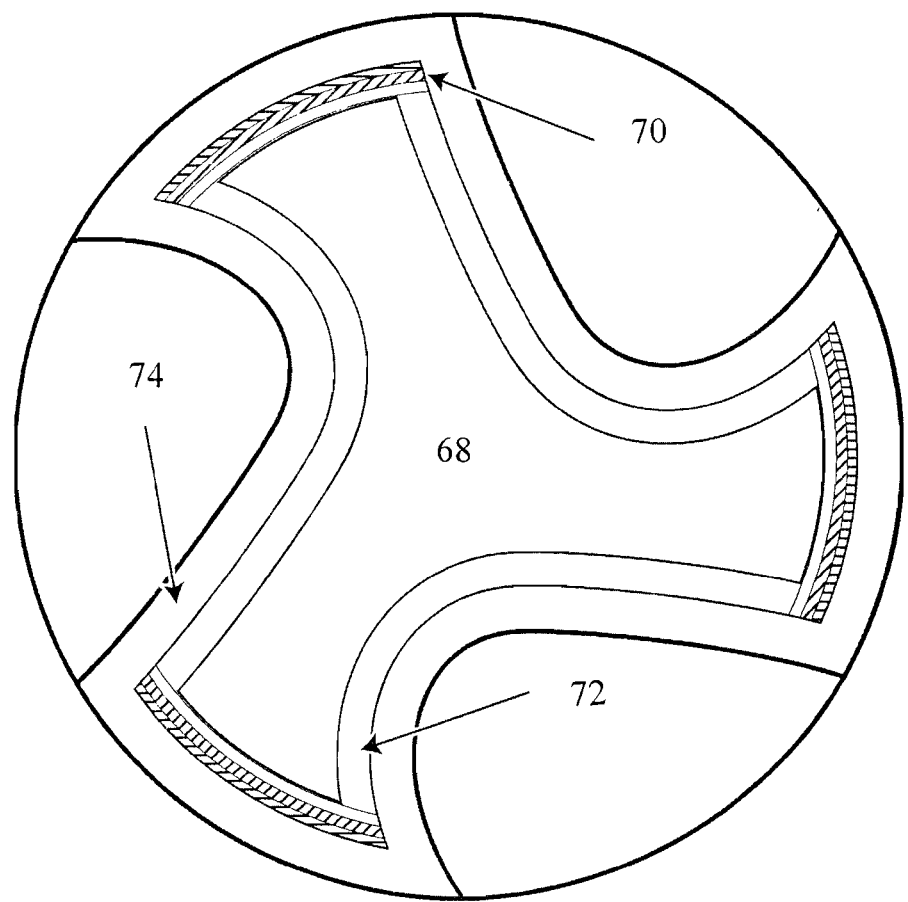

FIG. 10 shows different views of a scaler 60 having a core 62 made of 440XH martensitic stainless steel and subjected to dual processing treatment. First, the Ti/TiN multilayer cermet coating 64 having thickness of about 2 µm is deposited all over the blank blade (before sharpening). Then the blade is removed from the coating chamber and sharpens resulting in removing the coating from one side of the blade. After sharpening the blade may be heat treated to restore the maximum hardness of the core metal. After that stage the sharpened and optionally heat treated blade is cleaned by mild vibratory tumbling to remove the very top surface layer which maybe defective or contains some burrs and subjected to plasma immersion ionitrided treatment in low pressure auxiliary arc nitrogen plasma discharge. Since the coating 64 having diffusion barrier properties effectively blocking the nitrogen diffusion, the ionitrided layer 66 is formed only along the side of the blade where the coating was removed after the first coating cycle. FIG. 10c shows a cross-section A-A of the blade 60 shown in FIG. 10b. It can be seen that ionitrided layer forming on front side of the blade overlaps the nitride coating layer forming on opposite side of the blade.

FIG. 11 shows the cross sections of an implant drill 68 through all distinctive stages (a-d) of the surface engineering process producing a triplex coating architecture shown in FIG. 8c on a rotary dental instrument. FIG. 11a shows the cross-section of the blank drill (before the flute is ground) coated with Ti/TiN/TiCN/TiC multilayer gradient coating 70. FIG. 11b shows the same tool after grinding which produces a flute. FIG. 11c shows the drill after the first stage of the second coating process, which produces the ionitrided layer 72 on the inner side of the flute, where TiN coating was removed by grinding. FIG. 11d shows the final product, a triplex coated drill, having the top segment TBCN low friction anti-galling coating 74, which overlays the TiN on the outer side of the flute and ionitrided layer on the inner side of the flute.

In one of the preferred embodiments, a steel substrate has a bottom bondcoating segment of several vapour deposited layer pairs and is subsequently removed from the vacuum chamber of the filtered cathodic arc plasma depositing device and annealed or heat treated in vacuum or in a low pressure inert gas at a temperature between 900° C. and 1100° C. by usual methods, followed by quenching in nitrogen or nitrogen/argon atmosphere and tempering at 150° C. to 400° C. The coated and heat treated substrate then can be sharpened or ground to prepare a necessary cutting shape blade or flute. After this step, the substrate is cleaned by applying at least one finishing method selected from the group consisting of sandblasting, chemical cleaning, electrolytic cleaning, grinding, polishing, vibratory tumbling and ion etching to produce a cleaned substrate. The cleaned substrate the subjected to a subsequent coating deposition process to apply the overlay low friction, anti-galling coating, which reduces the stickiness between the rotary tool surface and the counterpart. The low friction coating is selected from the group containing carbides, carbo-nitrides, borides, and carbo-borides with an excessive amount of amorphous carbon forming a DLC type matrix. It can also be a doped or un-doped DLC layer. The hydrogenated DLC can be used for further reduction of the friction and stickiness between the instrument and the counterpart.

TABLE 1

| Item # | Metal Layer | Ceramic metal compound layer in combination with the metal, having desired wear resistant properties |
|---|---|---|
| 1 | Ti | TiC, TiN, Ti(CN), Ti(OCN) |
| 2 | Zr | ZrC, ZrN, Zr(CN), Zr(OCN) |
| 3 | V | VC, VN, V(CN), V(OCN) |
| 4 | Cr | CrN, CrC, CrCN |
| 5 | Hf | HfN |
| 6 | Mo | MoN |
| 7 | Nb | NbN, NbC |
| 8 | W | WC |
| 9 | Ti—Zr alloy | TiZrC, TiZrN, TiZr(CN), TiZr(OCN) |
| 10 | Ti—Cr alloy | TiCrC, TiCrN, TiCr(CN) |
| 11 | V—Ti alloy | VTiC, VTiN, VTi(CN) |
| 12 | Ti, Mo | TiMoN |
| 13 | Ti, Al | TiAlN, TiAlON |
| 14 | Ti, Al, Si | TiAlSiN |
| 15 | Ti, Nb | TiNbN |
| 16 | Al | AlN, Al$_2$O$_3$ |
| 17 | Ti, Cr | (Ti, Cr)B$_2$ |
| 18 | Ti | TiB$_2$ |
| 19 | Ti, Al | (Ti, Al)B$_2$ |

Table 2 lists the preferred metals and alloys used to obtain the appropriate top segment nanostructured coating having low friction and anti-galling properties in conjunction with the bottom bondcoating segment.

TABLE 2

| Item # | Elemental composition | Amorphous matrix composition | Nanocrystalline filling phase composition |
|---|---|---|---|
| 1 | C | Hydrogen free single layer DLC | None |
| 2 | C | Hydrogen free multilayer DLC, consisting of iC sublayers with different ratio of sp3/sp2 bonds and having different hardness | None |
| 3 | iCH | Hydrogenated DLC | None |
| 4 | Transition metal + C | Me doped DLC | MeC |
| 5 | Ti, B, C | Ti, B doped DLC | TiC, TiB$_2$, B$_4$C |
| 6 | Ti, Zr, B, C | Ti, Zr, B doped DLC | TiC, TiB$_2$, B$_4$C, ZrB$_2$, ZrC |
| 7 | B, C | B doped DLC | B$_4$C |
| 8 | B, C, H | B doped hydrogenated DLC | B$_4$C |
| 9 | Ti, Al, Cr, Mo, Zr, B, C, H | Ti, Al, Cr, Zr, Mo, B doped hydrogenated DLC | TiC, TiB$_2$, B$_4$C, ZrC TiC, (Ti, Al)B$_2$, (Ti, Cr)B$_2$, ZrB$_2$, Mo$_2$C |

The top layer can be also composed of cermet based material doped with lubricious metals such as silver, gold or a like. In this case the cermet provides a wear resistant tough anti-galling matrix with embedded lubricious metallic inclusions. One example of such coating is TiCN+Ag. Other examples include multiphase nanocrystalline carbides, carbo-nitrides, and borides with addition of silver and/or gold metallic inclusions. Alternatively, the lubricous metal coatings such as silver can be applied over the bondcoating layer as a replacement for DLC type top low friction segment, forming Me/MeN+Ag coating architecture. Another alternative solution for the low friction coating segment can be solid lubricant materials such as MoS$_2$ and WS$_2$. These solid lubricant compounds can be embedded into a hard coating matrix either in the bottom bondcoating or top coating segment. One example of such a nanocomposite self-lubricating coating is Ti/TiCN multilayer matrix with embedded WS$_2$ inclusions. This coating can be prepared by hybrid LAFAD-UBM process. In this process the LAFAD will be equipped with two targets made of transition metals such as Ti, Cr, V or a like or their alloys. The magnetron targets will be WS$_2$ or MoS$_2$. The reaction gas atmosphere will be formed by nitrogen or mixture of nitrogen with methane or other HC gas, while argon will be supplied in the vicinity of magnetron targets as a sputtering gas. The resulting coating will consist of hard cermet matrix with embedded MoS$_2$ or WS$_2$ solid lubricant phases.

The preferred substrate surface temperature during the cathodic arc plasma deposition steps is between 100 and 500° C. In some cases the temperature of the substrates to be coated cannot exceed a certain value; otherwise it can have a detrimental effect on the bulk metal properties. For example, temperature must be controlled in coating of rotary instruments made of cold work hardening steel such as AISI 300 series or NiTi nickel-titanium alloy. In case of instruments made of AISI 300 series stainless steel the bulk metal properties cannot be restored by appropriate post-deposition heat treatment. In the case of dental instruments such as endofiles made of NiTi shape memory alloy the temperature must not exceed 100°-300° C. during the coating process, otherwise post-deposition thermal-mechanical treatments are necessary to restore the shape memory properties of the instrument. In some cases the properties of the NiTi may not be able to be restored at all if, for example, the instrument is exposed to too high of a temperature for too long a period of time. For NiTi type substrates with thin part diameters exposure to temperatures as high as 350° C. or five minutes can degrade the shape memory effect of the material. At 300° C. this loss can occur in 20 minutes, one hour at 250° C., or 2 hours at 200° C. Both the coating of the substrate material, and post deposition heat treatment are meant to maintain the stiffness or increase the stiffness properties of the substrate when used in many applications. It is also important to notice that some of the coating layers, specifically the free carbon contained top low friction segment coatings are extremely sensitive to high temperature treatment in both oxidizing and reducing environments. Therefore heat treatment of these coatings is as problematic as the bulk metal substrates. In all these cases precise thermal management of the substrate in the vacuum plasma coating deposition process is required.

In a deep vacuum, the only cooling mechanisms are radiation and conduction cooling. Using the pulsing mode of the LAFAD plasma source the precise thermal management of the tiny instruments such as endofiles can be achieved by periodically interrupting the exposure of the instrument substrate to the vapor plasma environment. This can be accomplished by using a magnetic shutter which effectively closes the path of the vapor metal plasma flow toward the substrates to be coated. When the magnetic shutter is closed (the deflection magnetic system OFF) only the near neutral metal vapor flow generated by the EBPVD source or magnetrons will be deposited on the metal instrument substrate, bringing a negligible amount of heat, while the substrate is losing the thermal energy by radiation cooling. This allows the temperature of the substrate to be controlled during the deposition of the cermet coating at a desirable level and not to exceed the temperature which damages the bulk metal properties.

The duration time and duty cycle of the filtered arc source operation effectively determine the substrate temperature in the vacuum plasma deposition process of the cermet coating, while the total coating time determines the coating thickness. The periodic interruption of substrate exposure to metal vapor plasma flow can also be achieved by periodic turning on and off the plasma sources. Since substrate temperature is a very important parameter in determining film properties, special attention is paid to in-situ monitoring of substrate temperature using a high-precision pyrometers and built-in thermocouples.

Figure 9:
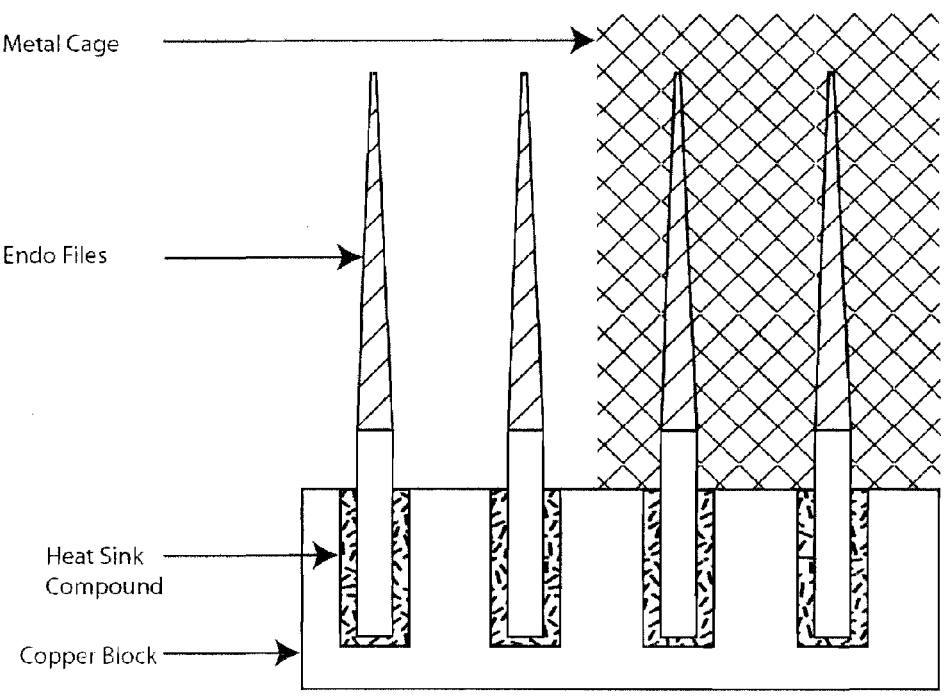
FIG. 9 is a set of NiTi endofiles installed into a substrate holder copper block with a thermal sink compound shown with or without a surrounding metal cage which absorbs ion energy.

In addition, the substrate rotary tools such as endofiles are installed into blocks having a high thermal capacity for heat transfer, these blocks may be made of copper, aluminum, or similar alloy, then a heat sink paste is used to provide appropriate heat transfer during the coating deposition process as shown in FIG. 9. If the thermal flux conveyed by the plasma to the instrument surface is q[W/cm$^2$] and the heat capacity of the tool is $C_t = c_t \times m_t$, where $c_t$ is specific heat capacity of the metal substrate, $m_t$ is mass of the instrument; then the pulse period $t_p$, when the instrument can be exposed to the vapor plasma deposition environment can be estimated as following:

$$t_p = (C_t \times (T_m - T_0))/q, \quad (1)$$

where $T_0$ is initial temperature of the instrument, which can be estimated as room temperature, $T_m$, is maximum temperature to which the instrument can be heated during vapor plasma deposition treatment. More thorough calculations must be provided to take in to account the radiation and conduction cooling of the instruments during pause time in the cycled deposition process. In this case the expression (1) still gives a first rough estimate of the maximum plasma exposure time. The total coating deposition process time is limited by the heat capacity of the substrate holder blocks made of copper, aluminum or other metal with suitable high thermal conductivity and heat capacity. When the temperature of substrate holder block $T_b > (2/3)T_m$, the coating deposition process must be interrupted until the temperature of the substrate holder block drops below this level.

Another way of trimming the substrate temperature below the value detrimental to bulk metal properties, is placing a substrate in a metallic or wire cage, which can effectively reduce the heat of the substrate due to intense ion bombardment as illustrated in FIG. 9. It is also possible to add Hydrogen or Helium gas to the chamber at certain intervals to reduce the chamber and substrate temperatures.

The technology described in this invention can be applied to wide variety of applications in forming and cutting tools, machine parts, medical and dental instruments and many others. In dental instruments applications it can be applied to both handle instruments such as regular and ultrasonic scalers, scalpels, needleholders and to rotating instruments such as root canal endofiles, dental drills and burs. The substrate dental instruments can be made of different type of steel and metal alloys. The preferable type of steel or metal alloy for different kind of dental instruments is shown in Table 3.

TABLE 3

Description of the metal alloys preferably used for the dental instruments of this invention.

| Item No. | Name of dental instrument | Preferable type of steel or metal alloy | Manufacturer of substrate metal | Composition of substrate metal |
|---|---|---|---|---|
| 1 | Scalers and Currettes | 1-- 440A, 440C, 440XH, 440F-Se; 2-1RK91, 13C26, 4C27Mo2, 20AP | 1-Carpenter 2-Sandvic by Bioline ™ brand | 440 series is high chromium bearing steel; 440E-Se composition: 0.95/1.20 C, 1.25 Mn, 0.040 P, 0.15 S or Se min., 1.00 Si, 16.00/18.00 Cr, 0.60 Mo, Bal. Fe |
| 2 | Ultrasonic scalers | 1-17-4 family, 13-8; 2-TrimRite, Trinamet, 420, 1RK91, 13C26, 4C27Mo2, 20AP, | 2-Sandvic by Bioline ™ brand | TrimRite composition: 0.15/0.30 C, 1.00 Mn, 0.04 P, 0.03 S, 1.00 Si, 13.50/15.00 Cr, 0.25/1.00 Ni, 0.40/1.00 Mo, Bal. Fe; Trinamet composition: Type Analysis Carbon (Maximum) 0.30% Manganese (Maximum) 1.00% Phosphorus (Maximum) 0.040% Sulfur (Maximum) 0.030% Silicon (Maximum) 1.00% Chromium 12.00 to 14.00% Molybdenum 1.00 to 3.00% Copper 2.00 to 3.00% Iron Balance |
| 3 | Implant drills | 1-17-4 family, 300 series; 2-1RK91, 13C26, 4C27Mo2, 20AP | 2-Sandvic by Bioline ™ brand | 1RK91 composition: C + N ≤ 0.05, Cr 12.0, Ni 9.0, Mo 4.0, Ti 0.9, Al 0.30, Si 0.15, Cu 2.0 7C27Mo2 composition: C 0.38, Si 0.4, Mn 0.6, P max 0.025, S max 0.01, Cr 13.5, Mo 1.0 20AP composition: C 1.0, Si 0.2, Mn 0.4, P max 0.03, S 0.05, Cr max 0.10, Ni max 0.10, Mo max 0.03, others Pb 0.2 |
| 4 | Dental burs | Cemented carbide | Brasseler, Sybron | |
| 5 | Root canal endofiles | 1-17-4, 13-8; 2-NiTi 3-TrimRite, Trinamet, 420, 1RK91, 13C26, 4C27Mo2, 20AP | 3-Sandvic by Bioline ™ brand | NiTi shape memory alloy has near equiatomic 50%/50% Nickel/Titanium composition |

Example 1

Stainless Steel Endofiles with Multilayer Gradient TiCR/TiCrN+TiCrCN+TiBC Coating A set of endofiles made of 17-4 stainless steel were installed into the substrate holders positioned on the satellites of the rotating table of surface engineering system shown in FIG. 1. The following process parameters were used for the deposition of TiCrN/TiCr—TiCrCN bottom segment and transitional layer by LAFAD plasma source equipped with two (opposite) Ti and Cr targets. The arc currents were set on approximately 100 amperes for both Ti and Cr targets. The auxiliary arc discharge current was set on 150 amperes during argon ion cleaning stage and then reduced to 40 amperes during coating deposition stage. The substrate temperature did not exceed 300° C. An Advanced Energy Industry MDX- II power supply coupled with a Sparkle-V accessory unit was used as a bias power supply. The bias voltage was set at 250 volts during an ion cleaning stage followed by 1000 volts during 2 mins of a metal ion etching stage. The pulse frequency during ion cleaning/etching stages was set at 48 kHz with 90% duty cycle (reverse pulse time 2 μs). The bias voltage during coating deposition stage was set at 60 volts DC. The TiCrN/TiCr multi-layer nanolaminated coating was deposited at $4 \times 10^{-2}$ Pa gas pressure with nitride sublayer being deposited in nitrogen reactive atmosphere and metallic sublayer being deposited in argon. Each bilayer in TiCrN/TiCr multilayer architecture was deposited during 10 min with 7 min dedicated to TiCrN and 3 min to TiCr sublayers. The rotation speed of the substrate platform was set at 9 rpm, which corresponds to a 3-4 nm bi-layer thickness in the (Ti based/Cr based) nanolaminated architecture, taking into account an approximately 1.5 μm/hr deposition rate for TiN and 1 μm/hr for CrN coatings deposited in single (one fold) rotation mode. The pure nitrogen was gradually changed to $N_2/40\%$ $CH_4$ during a 40 min deposition of the intermediate TiCrCN layer. The preliminary set of samples was prepared with a TiCrC upper tribological segment deposited by LAFAD, on top of the transition TiCrCN layer using acetylene as a reactive gas at pressure of 5 mTorr. During deposition of the bottom segment TiCr/TiCrN+TiCrCN coating the magnetic deflecting system was set in pulse mode with 50% duty cycle and frequency of 0.1 Hz, which result in 5 s deposition time followed by 5 s cooling time at each bi-period. The thickness of the bottom segment coating was 0.2 μm. Additional samples were produced with an upper layer consisting of TiBC nanocomposite cermet deposited by a hybrid filtered arc-unbalanced magnetron process. In this case both primary cathodic arc sources of LAFAD plasma source were equipped with Ti targets for generating titanium vapor plasma flow. The magnetron power density was set at approximately 5.5 $W/cm^2$. A small amount of reactive gas (methane) was added to argon at a total gas pressure of 0.2 Pa. For deposition of nanolaminated TiBC/iBC (NL) coating architecture the deflecting magnetic field of the LAFAD plasma source was cycled on for 5 s and off for 25 s. This setting resulted in the TiBC coating architecture consisting of TiBC sublayer of approximately 4 nm thickness followed by 1 nm of $B_4C$ sublayer per each bi-period across 1 μm of top segment TiBC coating. After the deposition process was finished the substrates were discharged from the chamber. It was found that substrate stainless steel files do not lose their stiffness after the multilayer coating process.

Example 2

NiTi Endofiles with Anti-Friction Carbon Diamond-Like Coating

A set of endofiles made of NiTi nickel-titanium alloy were placed in the copper blocks and installed in the substrate holders, positioned on the satellites of the rotating table of surface engineering system shown in FIG. 1. The thermal transfer or "thermal sink" compound ("Thermal Compound" Part #120-8, manufactured by Wakefield Engineering Inc. of MA) was placed in the hole to reduce the thermal contact resistance between the instrument and the copper block so that instruments can be provided with substantial thermal conduction cooling during vapour plasma deposition process.

The following process parameters were used for the deposition of DLC low friction carbon coating using two LAFAD plasma sources, one (for bondcoating layer) equipped with two Ti targets and another one equipped with two graphite targets. The ion cleaning step was performed in argon ionized in auxiliary arc discharge, created between primary cathodes of one LAFAD plasma source as an emitter of electrons and auxiliary anodes installed around the substrate table in a main vacuum chamber. The auxiliary anode current was 100 amperes, the argon pressure was 0.5 mtorr and bias voltage, created autopolarization of substrates under 13.56 MHz voltage provided by a RF generator, was 200 volts. The ion cleaning step lasts 2 min, which protects the substrates against overheating. After the ion cleaning step the deflecting magnetic field of LAFAD source with Ti targets was turned ON for deposition of the bond coating Ti/TiN/TiC layer. It was started from depositing of the 10 nm Ti layer followed by deposition of 30 to 50 nm of TiN layer in nitrogen and topped with 100 nm of TiC layer deposited in a methane reactive gas atmosphere. The gas pressure during deposition of the bondcoating is 0.5 mTorr, the auto-bias voltage is 50 volts.

After deposition of the bondcoating layer the LAFAD source with Ti targets was turned OFF and substrates were subjected to cooling step in helium or hydrogen at the pressure ranging from 1 to 10 mTorr. The duration of cooling step ranging from 10 min to 1 hr or more, depending upon thermal capacity of the substrates to be coated and substrate holder blocks. After the cooling step, the chamber was pumped down to 0.01 mTorr and other LAFAD source with graphite targets is turned ON. The 13.56 MHz RF bias power supply was connected to the substrate table instead of DC pulse bias power supply, used during deposition of cermet bond coating bottom segment. The substrate auto-bias during this stage was set at −50 volts. In addition the high voltage pulses having 2.5 kV amplitude, 25 μs width and 600 Hz repetition frequency were applied subsequent to the low auto-polarization bias voltage. During the DLC deposition step the LAFAD deflecting field was periodically turned off for 10 s and turned on for 5 s which results in the plasma deposition and heating of substrates with subsequent cooling. This approach is capable of precise thermal management of substrates in vapor plasma deposition processes. After 1 hr of DLC coating deposition step the LAFAD filter is turned off and substrates are discharged from the vacuum chamber. It is found that with approximately 1 μm of DLC coating the NiTi endofiles fully restored their shape memory, while torsional fatigue life was improved up to 200% due to reduction of friction and stickiness to the counterbody (bovine). Deposition of the top DLC layer having amorphous structure also results in substantial improvement of corrosion resistance by effectively filling the holes, voids and other imperfections and defects both on the substrate surface and in the bottom cermet layer, preventive it against pitting corrosion attacks.

Example 3

Endodontic Files Made of 17-4 Stainless Steel with Two Segment Cermet-DLC Coating A set of blank endofiles made of 17-4 stainless steel is cleaned by vibratory tumbling followed by ultrasonic cleaning dried and then loaded in the surface engineering system shown in FIG. 1. The surface finish of the blank endofile after cleaning is better than Rms<20 nm. The first bondcoating segment consisting of TiZr/TiZrN multilayer+TiZrCN transition layer+TiZrC top layer is deposited on the blanks. The coating deposition process is performed using the LAFAD plasma source with Ti and Zr targets installed into opposite primary cathodic arc sources. The coating deposition parameters are largely the same as described before in Example 1. The coating thickness is 2 μm. After finishing the deposition of the bondcoating segment the substrates endofiles are removed from the chamber and subjected to heat treatment to restore the bulk mechanical properties, the primary of which is to retain the hardness and stiffness properties. After heat treatment the coated blanks are subjected to grinding and polishing treatment to make a flute with a cutting edge. As a result of this step the outer side of said flute remains coated with a 2 μm thick bottom bondcoating segment and the other (inner) side of said flute is uncoated, while the very tip of the cutting edge is entirely made of the bondcoating multilayer cermet, having a hardness of H≥25 GPa. This step forms a cutting flute with a metallic underside and a ceramic metal outer layer or top side. After that the instruments are subjected to chemical-mechanical vibratory tumbling which creates a fine surface finish on the uncoated side of the flute and does not affect the outer side of the flute and the very tip of the cutting edge which are much harder than vibratory tumbling media. After that the substrate instruments are ultrasonically cleaned and placed in the copper blocks positioned on the satellites of the rotating table of surface engineering system shown in FIG. 1. The thermal transfer or "thermal sink" compound ("Thermal Compound" Part #120-8, manufactured by Wakefield Engineering Inc. of MA) is placed in the hole to reduce the thermal contact resistance between the instrument and the copper block so that the instruments will have substantial thermal conduction cooling during vapour plasma deposition process. After ion cleaning and 5 min of exposure to TiZr metal vapor plasma in methane reactive gas atmosphere at 1 mtorr and −100V bias for deposition of thin TiZrC sublayer, the LAFAD source deflecting field is turned off and remains in electron emission auxiliary arc mode for ionizing gaseous plasma in the main chamber. At this moment methane flow rate is reduced to 4 sccm, argon is added as a main balance gas to reach 1 mtorr operating pressure, two unbalanced magnetrons with $B_4C$ targets are turned on and high voltage (12 kV) pulse bias is imposed on the substrates to provide boron-carbon ion implantation of the uncoated and coated sizes of the flute. This stage continues for 10 minutes followed by deposition of nanolaminated TiZrBC coating containing large amount of free amorphous carbon by periodically exposing the substrates to TiZr metal vapor flow when deflection magnetic field of LAFAD source is turned on and continuous exposure of the substrates to $B_4C$ magnetron sputtering flow and additional hydrocarbon plasma flow at −50 volts bias. This results in deposition of a low friction non-stick TiCrBC top coating segment, which effectively encapsulates the smooth metallic surface of the inner side of the flute and provides large improvement of fatigue life by securing low torque momentum and preventing the development and fast propagation of surface microcracks. At the same time this coating design has demonstrated cutting efficiency by retention of the wear and corrosion resistant low friction anti-galling dual ceramic cutting edge of the flute. Using 3MS reactive gas in addition to nitrogen during deposition of the top low friction segment coating results in TiCrB-SiCN composition which further improves the corrosion resistance and cutting efficiency of the entire surface engineering of this type of dental instruments.

Example 4

Endodontic Files Made from NiTi Alloy with 2-Segment Cermet+DLC Coating

In this process the blank endofiles without flutes made of NITINOL or 50/50 at % NiTi alloy are subjected to deposition of a relatively thick TiCr/TiCrN/TiCrCN/TiCrC multilayer gradient cermet coating 2 μm thick at the first stage of the surface engineering process. During deposition of the bottom bond coating segment the temperature of the endofile substrates can reach up to 500° C., which effectively erases the shape memory properties. After this stage the coated blanks are removed from the LAFAD surface engineering chamber and subjected to annealing heat treatment stage. During this stage the coated blank files are subjected to 30 min heating at 1100° C. in nitrogen (99.995 purity) followed by rapid cooling by immersing the boat with files into ice. After annealing the coated blank files are subjected to thermal-mechanical treatment stage consisting of grinding by fine diamond wheels in a multi-step grinding-tempering process. Alternatively, after annealing and rapid quench the files can be subjected to tempering at temperatures ranging from 400 to 650° C. for time duration ranging from 15 min to 2 hrs. During this process the files are subjected in turn to grinding and tempering in a tempering furnace which allows restoring its shape memory properties. After this stage the files, which now have a flute are cleaned by mild vibratory tumbling and loaded second time in the LAFAD coating chamber for the subsequent deposition of hydrogen free DLC coating. This process is provided by LAFAD plasma source shown in FIG. 1, which is equipped with two graphite primary cathodic targets. The substrate endofiles are installed with double rotation capability into copper blocks with thermal sink compound. No plasma creating gases are used in this process and the chamber pressure during DLC process is measured at about 0.01 mtorr. The substrates are subjected to floating bias potential with superimposed high voltage pulses of 2 kV amplitude, 25 μs duration and 1000 Hz repetition frequency. The duration of this dual filtered arc deposition process is 4o min resulting in deposition of 0.25 μm DLC layer, which overlays the bottom bond coating cermet layer on the outer side of the flute and uncoated NiTi alloy on the inner side of the flute. The hardness of the DLC layer deposited on NiTi alloy was measured by means of nanoindentation as 25 GPa. The cumulative compressive stress in combined cermet+DLC coating was measured as about 3 GPa.

A novel coating is described that protects the coated surface against wear and corrosion while providing a low friction, anti-galling surface. In the exemplified embodiment, this novel coating architecture of a multilayer metal/ceramic bondcoat topped with a non-friction, anti-galling top coat is applied to rotary tools for dental and medical applications. It is important to note however that the subject coating can be effectively applied to other dental and surgical instruments including, but not limited to, saw blades, scalers, curettes, scissors, razorblades, scalpels, orthodontic components, burs, and implants. Additionally, the subject coating and the method of temperature control described for applying the coating are intended to be used for coating ultrasonic cutting, debriement, surgical, and periodontal therapy tools or instruments both of Piezo and Magneto Restrictive types for dental and medical applications. Finally the coatings and methods of the subject invention can be applied to other industries, such as the aerospace industry, the automotive industry (for use on, for example, gears, bearings, combustion engine components such as pistons and piston rings, valves etc.) and other cutting and forming tools industries (for example, for use on dies and molds).

It is understood that the foregoing examples are merely illustrative of the present invention. Certain modifications of the articles and/or methods may be made and still achieve the objectives of the invention. Such modifications are contemplated as within the scope of the claimed invention.

The invention claimed is:

1. A method for producing a wear resistant cutting edge, the method comprising the steps of:
   i) providing a substrate capable of electrical conduction, having a surface and cleaning said surface with at least one cleaning method selected from the group consisting of chemical cleaning, electrolytic cleaning, grinding, polishing, tumbling and ion bombardment to produce a cleaned substrate;
   ii) placing the cleaned substrate into a vacuum chamber of a vapour depositing device capable of providing controlled electric and magnetic fields, and having a substrate holder capable of holding at least one substrate, a target electrode holder, and an inlet for a vapour depositing atmosphere of controlled composition and pressure;
   iii) providing a target electrode within the vacuum chamber, of at least one of the metals selected from the group consisting of titanium, chromium, vanadium, aluminum, molybdenum, niobium, tungsten, hafnium, zirconium, and alloys thereof;
   iv) providing a vapour depositing atmosphere within said vacuum chamber, comprising at least one of the gases selected from the group consisting of argon, neon, xenon, krypton and helium;
   v) applying electric potential and a filtering magnetic field in an atmosphere within the vacuum chamber, to obtain a first, vapour deposited metal layer selected from the group consisting of titanium, chromium, vanadium, aluminum, molybdenum, niobium, tungsten, hafnium, zirconium, and alloys thereof, on the surface of the substrate;
   vi) applying electric potential and a filtering magnetic field in an atmosphere within the vacuum chamber, containing at least one of the gases selected from the group consisting of nitrogen, methane or other hydrocarbon gas, borazin, 3MS gas or oxygen, to obtain a second, vapour deposited layer of a ceramic compound of a metal selected from the group consisting of titanium, chromium, vanadium, aluminum, molybdenum, niobium, tungsten, hafnium, zirconium, and alloys thereof, on the first layer deposited on the surface of the substrate;
   vii) repeating steps v) and vi), thereby obtaining multiple vapour deposited metal layers and multiple vapour deposited ceramic compound layers on said surface of the substrate;
   viii) heat treating the substrate with multiple vapour deposited metal layers and multiple vapour deposited ceramic compound layer on its surface to restore bulk mechanical properties of the substrate;
   ix) depositing a top coat by a vapor deposition process overlaying the metal-ceramic coating, the top coat comprising an amorphous diamond-like matrix selected from the group consisting of carbon, silicon, nitrogen, hydrogen, oxygen and transition metals;
   x) removing the substrate having multiple vapour deposited metal and ceramic layers on the substrate surface, from the vapour depositing device; and
   xi) sharpening the substrate by grinding and/or polishing to develop at least one side of at least one cutting edge; wherein the multiple vapour deposited metal layers and multiple vapour deposited ceramic compound layers obtained in step vii) have a hardness of greater than 20 gigapascals and a toughness of greater than $0.05\ H^3/E^{*2}$, the amorphous diamond-like matrix containing top coat of step ix) has nanocrystals sized from 1 to 100 nanometers and a friction coefficient of less than 0.3, and wherein the top coat imposes a compressive stress of from 0.1 to 8 gigapascals.

2. The method of claim 1, further comprising the step of, after step x) heat treating said obtained metal and ceramic vapour deposited coating layers and said vapor deposited top coat on said substrate surface.

3. The method of claim 1, wherein the temperature of said substrate is controlled by a method selected from the group consisting of exposing said substrate to plasma deposition in a periodic pulsing manner, providing thermal transfer elements, providing thermal transfer paste, providing screens to shield said substrate, providing shutters to control exposure of said substrate to plasma deposition and injecting gasses into said chamber to dissipate heat.

4. The method of claim 1, wherein said substrate is Bioline 1RK91 stainless steel.

5. A method for producing a wear-resistant cutting edge, the method comprising the steps of:
   i) providing a blank (unsharpened) substrate capable of electrical conduction by applying at least one finishing method selected from the group consisting of sandblasting, chemical cleaning, electrolytic cleaning, grinding, polishing, vibratory tumbling and ion etching to produce a cleaned substrate;
   ii) sharpening the substrate by grinding and/or polishing to develop at least one side of at least one cutting edge;
   iii) cleaning the sharpened substrate by applying at least one finishing method selected from the group consisting of sandblasting, chemical cleaning, electrolytic cleaning, grinding, polishing, vibratory tumbling and ion etching to produce a cleaned sharpened substrate;
   iv) depositing a metal-ceramic coating on the cleaned sharpened substrate by a vapor deposition process, the metal-ceramic coating comprising at least one pair of a metallic layer selected from the group consisting of titanium, chromium, vanadium, aluminum, molybdenum, niobium, tungsten, hafnium, zirconium, and alloys thereof; overlayed by a ceramic layer selected from the group consisting of nitrides, carbides, oxycarbides, oxynitrides, borides, carboborides, borocarbonitrides, silicides, borosilicides and combinations thereof;
   v) heat treating the cleaned, sharpened metal-ceramic coated substrate to restore bulk mechanical properties of the substrate; and
   vi) depositing a top coat by a vapor deposition process overlaying the metal-ceramic coating, the top coat comprising an amorphous diamond-like matrix selected from the group consisting of carbon, silicon, nitrogen, hydrogen, oxygen and transition metals; wherein the metal-ceramic coating of step iv) has a hardness of greater than 20 gigapascals and a toughness of greater than $0.05\ H^3/E^{*2}$, the top coat of step vi) has nanocrystals sized from 1 to 100 nanometers and a friction coefficient of less than 0.3, and wherein the top coat imposes a compressive stress of from 0.1 to 8 gigapascals.

6. The method of claim 5, wherein said blank (unsharpened) substrate is sharpened to be a dental tool selected from the group consisting of a scaler, an endofile and an implant drill.

7. The method of claim 5, wherein said substrate is Bioline 1RK91 stainless steel.

8. A method for producing a wear-resistant cutting edge, the method comprising the steps of:
   i) providing a blank (unsharpened) substrate capable of electrical conduction by applying at least one finishing method selected from the group consisting of sandblasting, chemical cleaning, electrolytic cleaning, grinding, polishing, vibratory tumbling and ion etching to produce a cleaned substrate;

ii) depositing a metal-ceramic coating on the cleaned blank substrate by a vapor deposition process, the metal-ceramic coating comprising at least one pair of a metallic layer selected from the group consisting of titanium, chromium, vanadium, aluminum, molybdenum, niobium, tungsten, hafnium, zirconium, and alloys thereof; overlayed by a ceramic layer selected from the group consisting of nitrides, carbides, oxycarbides, oxynitrides, borides, carboborides, borocarbonitrides, silicides, borosilicides and combinations thereof;

iii) heat treating the cleaned, metal-ceramic coated blank substrate to restore bulk mechanical properties of the substrate;

iv) sharpening the substrate by grinding and/or polishing to develop at least one side of at least one cutting edge;

v) cleaning the sharpened substrate by applying at least one finishing method selected from the group consisting of sandblasting, chemical cleaning, electrolytic cleaning, grinding, polishing, vibratory tumbling and ion etching to produce a cleaned sharpened substrate;

vi) depositing a top coat by a vapor deposition process overlaying the metal-ceramic coating, the top coat comprising an amorphous diamond-like matrix selected from the group consisting of carbon, boron, silicon, nitrogen, hydrogen, oxygen and transition metals; wherein the metal-ceramic coating of step ii) has a hardness of greater than 20 gigapascals and a toughness of greater than 0.05 $H^3/E^{*2}$, the top coat of step vi) has nanocrystals sized from 1 to 100 nanometers and a friction coefficient of less than 0.3, and wherein the top coat imposes a compressive stress of from 0.1 to 8 gigapascals.

9. The method of claim 8, further comprising the step of, after step v) and before step vi) treating said cleaned substrate by a process selected from the group consisting of ionitriding, oxy-nitriding, ion implantation and carburizing.

10. The method of claim 8, wherein said blank (unsharpened) substrate is sharpened to be a dental tool selected from the group consisting of a scaler, an endofile and an implant drill.

11. The method of claim 8, wherein said substrate is Bioline 1RK91 stainless steel.

12. A method for producing a wear-resistant cutting edge, the method comprising the steps of:

i) providing a blank (unsharpened) substrate capable of electrical conduction by applying at least one finishing method selected from the group consisting of sandblasting, chemical cleaning, electrolytic cleaning, grinding, polishing, vibratory tumbling and ion etching to produce a cleaned substrate;

ii) depositing a metal-ceramic coating on the cleaned blank substrate by a vapor deposition process, the metal-ceramic coating comprising at least one pair of a metallic layer selected from the group consisting of boron, silicon, titanium, chromium, vanadium, aluminum, molybdenum, niobium, tungsten, hafnium, zirconium, and alloys thereof; overlayed by a ceramic layer selected from the group consisting of nitrides, carbides, oxycarbides, oxynitrides, borides, carboborides, borocarbonitrides, silicides, borosilicides and combinations thereof;

iii) heat treating the metal-ceramic coated blank substrate to restore bulk mechanical properties of the substrate;

iv) sharpening the substrate by grinding and/or polishing to develop at least one side of at least one cutting edge;

v) cleaning the sharpened substrate by applying at least one finishing method selected from the group consisting of sandblasting, chemical cleaning, electrolytic cleaning, grinding, polishing, vibratory tumbling and ion etching to produce a cleaned sharpened substrate; and vi) depositing a top coat by a vapor deposition process overlaying the metal-ceramic coating, the top coat comprising an amorphous diamond-like matrix selected from the group consisting of carbon, silicon, nitrogen, hydrogen, oxygen and transition metals; wherein the metal-ceramic coating of step ii) has a hardness of greater than 20 gigapascals and a toughness of greater than 0.05 $H^3/E^{*2}$, the top coat of step vi) has nanocrystals sized from 1 to 100 nanometers and a friction coefficient of less than 0.3, and wherein the top coat imposes a compressive stress of from 0.1 to 8 gigapascals.

13. The method of claim 12, further comprising the step of, after step v) and before step vi) treating said cleaned substrate by a process selected from the group consisting of ionitriding, oxy-nitriding, ion implantation and carburizing.

14. The method of claim 12, wherein said substrate is Bioline 1RK91 stainless steel.

15. The method of claim 12, wherein said blank (unsharpened) substrate is sharpened to be a dental tool selected from the group consisting of a scaler, an endofile, a dental bur, a scalpel and an implant drill.

* * * * *